(12) United States Patent
Deng et al.

(10) Patent No.: US 7,402,670 B2
(45) Date of Patent: Jul. 22, 2008

(54) SYNTHESIS BY CHIRAL DIAMINE-MEDIATED ASYMMETRIC ALKYLATION

(75) Inventors: Xiaohu Deng, San Diego, CA (US); Neelakandha Mani, San Diego, CA (US)

(73) Assignee: Janssen Pharmaceutica, N.V., Beerse (BE)

( * ) Notice: Subject to any disclaimer, the term of this patent is extended or adjusted under 35 U.S.C. 154(b) by 241 days.

(21) Appl. No.: 11/237,185

(22) Filed: Sep. 28, 2005

(65) Prior Publication Data

US 2006/0069250 A1    Mar. 30, 2006

Related U.S. Application Data

(60) Provisional application No. 60/614,816, filed on Sep. 30, 2004.

(51) Int. Cl.
C07D 225/00 (2006.01)
C07D 223/00 (2006.01)
C07D 211/00 (2006.01)
C07D 207/00 (2006.01)
C07D 205/00 (2006.01)
C07D 203/04 (2006.01)
C07D 321/00 (2006.01)

(52) U.S. Cl. .................. 540/450; 540/484; 546/184; 548/400; 548/950; 549/200

(58) Field of Classification Search .............. 540/450, 540/484; 546/184; 548/400, 950; 549/200
See application file for complete search history.

(56) References Cited

OTHER PUBLICATIONS

Beak et al. "Regioselective, Diastereoselective, and Enantioselective Lithiation-Substitution Sequences: Reaction Pathways and Synthetic Applications" Acc. Chem. Res. 1996, vol. 29, pp. 552-560.*
Beak, Peter et al 'Complex Induced Proximity Effects: Enantioselective Syntheses Based on Asymmetric Deprotonations of N-Boc-Pyrrolidines' J. Am. Chem. Soc. (1994), vol. 116, pp. 3231-3239.
Beak, Peter et al 'Regioselective, Diastereoselective, and Enantioselective Lithiation-Substitution Sequences: Reaction Pathways and Synthetic Applications' Acc. Chem. Res. (1996), vol. 29, pp. 552-560.
Arrasate, S. et al., "Synthesis of enantiomerically enriched β-amino alcohol derivatives via asymmetric lithiation of O-benzyl carbamates-imine addition using (−)-sparteine complexes," Tetrahedron: Asymmetry 2002, 13, 311-316.
Bachi, M.D. et al., "Synthesis of α-alkylidene-γ-lactones by intramolecular addition of alkoxycarbonyl free-radicals to acetylenes," Tetrahedron Lett. 1986, 27, 641-644.
Beak, P. et al., "α-Lithioamine synthetic equivalents: syntheses of diastereoisomers from Boc derivatives of cyclic amines," J. Org. Chem. 1993, 58, 1109-1117.
Campos, K.R. et al., "Enantioselective, Palladium-Catalyzed α-Arylation of N-Boc-pyrrolidine," J. Am. Chem. Soc. 2006, 128, 3538-3539.
Cardillo, G. et al., "Endomorphin-1 Analogues Containing β-Proline Are μ-Opioid Receptor Agonists and Display Enhanced Enzymatic Hydrolysis Resistance," J. Med. Chem. 2002, 45, 2571-2578.
Carey, F.A. and R.J. Sundberg, Advanced Organic Chemistry, Part A, 3rd ed. (1993), pp. 157-163.
Christoph, G. et al., "Asymmetric Synthesis of 2-Alkenyl-1-cyclopentanols via Tin-Lithium Exchange and Intramolecular Cycloalkylation," Org. Lett. 2002, 4, 2189-2192.
Danilewicz, J.C. et al., "Design of Selective Thrombin Inhibitors Based on the (R)-Phe-Pro-Arg Sequence," J. Med. Chem. 2002, 45, 2432-2453.
Dearden, M.J. et al., "A Readily-Accessible (=)-Sparteine Surrogate," J. Am. Chem. Soc. 2002, 124, 11870-11871.
Deng, X. et al., "Boron trifluoride etherate-assisted ring opening of ethylene oxide by a chiral organolithium: enantioselective synthesis of (R)-N-Broc-2-(2-hydroxyethyl)pyrrolidine," Tetrahedron: Assymmetry 2005, 16, 661-664.
DeVita, R.J. et al., "Investigation of the 4-O-Alkylamine Substituent of Non-Peptide Quinolone GnRH Receptor Antagonists," Bioorg. Med. Chem. Lett. 1999, 9, 2621-2624.
Dieter, R.K. et al. "Stereospecific coupling of α-aminoalkylcuprates with vinyl iodides," Tetrahedron Lett. 1997, 38, 5937-5940.
Dieter, R.K. et al., "Conjugate Addition Reactions of α-Aminoalkylcuprates with α,β-Alkenyl-, α,β-Alkynyl-, α,β-β,γ-Allenyl-, and α,β-γ,δ-Dienyl Carboxylic Acid Derivatives, Nitriles, and Sulfoxides," J. Org. Chem. 2000, 65, 8715-8724.
Hayakawa, Y. et al., "Structure of lydicamycin, a new antibiotic of a novel skeletal type," Tetrahedron Lett. 1991, 32, 213-216.
Hoppe, D. et al., "Enantioselective synthesis with lithium/(−)-sparteine carbonion pairs," Angew. Chem. Int. Ed. Engl. 1997, 36, 2282-2316.
Johnson, T.A. et al., "Asymmetric Carbon-Carbon Bond Formations in Conjugate Additions of Lithiated N-Boc Allylic and Benzylic Amines to Nitroalkenes: Enantioselective Synthesis of Substituted Piperidines, Pyrrolidines, and Pyrimidinones," J. Am. Chem. Soc. 2002, 124, 11689-11698.
Johnson, T.A. et al., "Asymmetric Carbon-Carbon Bond Formations by Conjugate Additions of Lithiated N-Boc Allylic Amines to Nitroalkenes: Enantioselective Synthesis of Functionalized Cyclopentanoids," Org. Lett. 2002, 4, 2747-2749.
Kise, N. et al., "Formation and reaction of 2-metalated N-Boc-4,4-dimethyl-1,3-oxazolidines in the presence of (−)-sparteine: new chiral formyl anion equivalents," Tetrahedron: Asymmetry 1998, 9, 3125-3128.
Laumer, J.M. et al., "Enantioselective Synthesis of 2-Substituted 2-Phenylethylamines by Lithiation-Substitution Sequences: Synthetic Development and Mechanistic Pathway," J. Org. Chem. 2002, 67, 6797-6804.
Leyendecker, F. et al., "Ligand effects in enantioface differentiating 1,4 addition to 1,3 diphenyl-2 propen-1 one," Tetrahedron Lett. 1983, 24, 3513-3516.

(Continued)

*Primary Examiner*—Kamal Saeed
*Assistant Examiner*—Joseph R Kosack

(57) ABSTRACT

Chiral synthesis from an achiral starting material by chiral diamine-mediated, such as sparteine-mediated, intermolecular asymmetric alkylation with a strained cyclic ether in the presence of a Lewis acid.

36 Claims, No Drawings

OTHER PUBLICATIONS

Lim, S.H. et al., "Kinetic Resolution of Racemic Lactones by Conjugate Additions of Allylic Organolithium Species: Direct Formation of Three Contiguous Centers with High Diastereo- and Enantioselectivities," Org. Lett. 2002, 4, 2657-2660.

Lovell, P.J. et al., "A Novel, Potent, and Selective 5-HT7 Antagonist: (R)-3-(2-(2-(4-Methylpiperidin-1-yl)ethyl)pyrrolidine-1-sulfonyl)phenol (SB-269970)," J. Med. Chem. 2000, 43, 342-345.

Manthorpe, J.M. et al., "Stereoselective Generation of E- and Z-Distributed Amide Enolates. Reductive Enolate Formation from Bicyclic Thioglycolate Lactams," J. Am. Chem. Soc. 2001, 123, 2091-2092.

Metallinos, C. et al., "(−)-Sparteine-Mediated Metalation of Ferrocenesulfonates. The First Case of Double Asymmetric Induction of Ferrocene Planar Chirality," Org. Lett. 2002, 4, 1935-1938.

O'Neil, I.A. et al., "The synthesis of a novel benzodiazocine via an intramolecular Staudinger/aza-Wittig cyclization," Tetrahedron Lett. 1997, 38, 3609-3610.

Pell, A.S. et al., "Measurements of heats of combustion by flame calorimetry. III. Ethylene oxide, trimethyl oxide, tetrahydrofuran, and tetrahydropyran," Trans. Faraday Soc. 1965, 61, 71-77.

Sasaki, H. "Oxetanes: Curing Properties in Photo-Cationic Polymerization," Experience the World of UV/EB, RadTech 2000: The Premier UV/EB Conference & Exhibition, Technical Conference Proceedings, Baltimore, MD, United States, Apr. 9-12, 2000, 61-68.

Stanchev, S. et al., "Synthesis, absolute configuration and circular dichroism of some diarylmethane derivatives," Tetrahedron: Asymmetry 1995, 6, 183-198.

Stapper, C. et al., "Total Synthesis of (=)-Dihydrocuscohygrine and Cuscohygrine," J. Org. Chem. 2002, 67, 6456-6460.

Takahashi, H. et al., "Synthesis and absolute configuration of optically pure (S)- and (R)-diarylmethylamines," Chem. Pharm. Bull. 1983, 31, 2183-2191.

Takahata, H. et al., "A New Synthesis of All Four Stereoisomers of 2-(2,3-Dihydroxypropyl)piperidine via Iterative Asymmetric Dihydroxylation To Cause Enantiomeric Enhancement. Application to Asymmetric Synthesis of Naturally Occurring Piperidine-Related Alkaloids," J. Org. Chem. 1999, 64, 8594-8601.

Vernier, J.-M. et al., "4-[[2-(1-Methyl-2-pyrrolidinyl)ethyl]thio]-phenol Hydrochloride (SIB-1553A): A Novel Cognitive Enhancer with Selectivity for Neuronal Nicotinic-Acetylcholine Receptors," J. Med. Chem. 1999, 42, 1684-1686.

Yamaguchi, N. et al., "An efficient method for the alkynylation of oxiranes using alkynyl boranes," Tetrahedron Lett. 1983, 24, 391-394.

Lectures 2 and 3: Structure and Confirmation, http://www.chm.bris.ac.uk/aldergroup/level3/ch300123.htm, visited Dec. 11, 2003.

The Merck Index, 13th ed. (2001), entry #8810, pp. 1557-1558.

* cited by examiner

SYNTHESIS BY CHIRAL DIAMINE-MEDIATED ASYMMETRIC ALKYLATION

This application claims the benefit of U.S. provisional application Ser. No. 60/614,816, filed on Sep. 30, 2004, which is incorporated herein by reference in its entirety.

FIELD OF THE INVENTION

The invention relates to novel synthetic methods that utilize chiral diamine-mediated asymmetric alkylation to generate chiral compounds. This asymmetric alkylation is achieved in the presence of a chiral diamine, a Lewis acid, and a cyclic ether.

BACKGROUND OF THE INVENTION

Chiral, non-racemic alkylated derivatives, including but not limited to chiral hydroxy-alkyl derivatives, of nitrogen-containing heterocycles such as pyrrolidine, are desirable for preparing a variety of compounds, including pharmaceutically active compounds. Chiral hydroxy-alkyl derivatives of nitrogen-contining heterocycles are typically needed in large quantities and good enantiomeric excess (ee) in drug discovery efforts. These derivatives are useful precursors in the synthesis of compounds such as Anthramycin, Lydicamycin, Halosaline, and Cuscohygrine, and also in the synthesis of many bioactive molecules, such as clemastine (antihistamine), (R)-3-(2-(2-(4-methylpiperidin-1-yl)-ethyl)pyrrolidine-1-sulfonyl)phenol (a 5-HT$_7$ receptor modulator), and SB-269970 (5HT$_7$ receptor antagonist). See, for example, O'Neil, I. A., Murray, C. L., Potter, A. J., Kalindjian, S. B., *Tetrahedron Lett.* 1997, 38, 3609-3610; Hayakawa, Y., Kanamaru, N., Morisaki, N., Seto, H., Furihata, K., *Tetrahedron Lett.* 1991, 3, 213-216; Takahata, H., Kubota, M., Ikota, N., *J. Org. Chem.* 1999, 64, 8594-8601; Stapper, C., Blechert, S., *J. Org. Chem.* 2002, 67, 6456-6460; Manthorpe, J. M., Gleason, J. L., *J. Am. Chem. Soc.* 2001, 123, 2091-2092; Danilewicz, J. C., Abel, S. M., Brown, A. D., Fish, P. V., Hawkeswook, E., Holland, S. J., James, K., McElroy, A. B., Overington, J., Powling, M. J., Rance, D. J., *J. Med. Chem.* 2002, 45, 2432-2453; Stanchev, S., Rakovska, R., Berova, N., Snatzke, G., *Tetrahedron: Asymmetry* 1995, 6, 183-198; Lovell, P. J., Bromidge, S. M., Dabbs, S., Duckworth, D. M., Forbes, I. T., Jennings, A. J., King, F. D., Middlemiss, D. N., Rahman, S. K., Saunders, D. V., Collin, L. L., Hagan, J. J., Riley, G. J., Thomas, D. R., *J. Med. Chem.* 2000, 43, 342-345; Cardillo, G., Gentilucci, L., Qasem, A. R., Sgarzi, F., Spampinato, S., *J. Med. Chem.* 2002, 45, 2571-2578; Vernier, J-M, El-Abdellaoui, H., Holsenback, H., Cosford, N. D. P., Bleicher, L., Barker, G., Bontempi, B., Chavez-Noriega, L., Menzaghi, F., Rao, T. S., Reid, R., Sacaan, A. I., Suto, C., Washburn, M., Lloyd, G. K., McDonald, I. A., *J. Med. Chem.* 1999, 42, 1684-1686; DeVita, R. J., Goulet, M. T., Wyvratt, M. J., Fisher, M. H., Lo, J-L, Yang, Y. T., Cheng, K., Smith, R. G., *Bioorg. Med. Chem. Lett.* 1999, 9, 2621-2624. One example of such chiral hydroxy-alkyl derivatives of N-containing heterocycles is (2R)-2-(2-hydroxy-ethyl)-pyrrolidine-1-carboxylic acid tert-butyl ester, also known as (+)-(2R)-1-Boc-2-(2-hydroxy-ethyl)-pyrrolidine, a compound of formula (Ia), or its deprotected form, a compound of formula (Ia'):

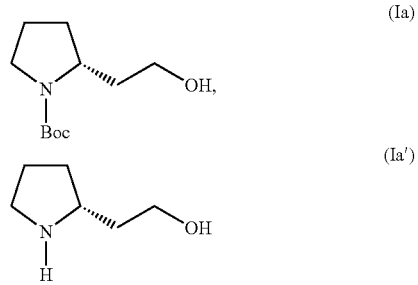

Conventional methods to synthesize chiral hydroxy-alkyl derivatives of nitrogen-containing heterocycles, such as a compound of formula (Ia), involve multiple step sequences from starting materials that are themselves chiral, and often expensive, such as D-prolinol or D-proline. Suitable chiral starting materials having nitrogen-containing heterocycles with rings smaller or larger than five members are often not commercially available. These starting materials, however, are not regarded as being suitable for large-scale synthesis. See, for example, O'Neil, I. A.; Murray, C. L.; Potter, A. J., Kalindjian, S. B., *Tetrahedron Lett.* 1997, 38, 3609-3610; Lovell, P. J.; Bromidge, S. M., Dabbs, S., Duckworth, D. M.; Forbes, I. T.; Jennings, A. J.; King, F. D.; Middlemiss, D. N.; Rahman, S. K.; Saunders, D. V.; Collin, L. L.; Hagan, J. J., Riley, G. J., Thomas, D. R., *J. Med. Chem.* 2000, 43, 342-345; Cardillo, G., Gentilucci, L., Qasem, A. R., Sgarzi, F., Spampinato, S., *J. Med. Chem.* 2002, 45, 2571-2578; Vernier, J-M, El-Abdellaoui, H., Holsenback, H., Cosford, N. D. P., Bleicher, L., Barker, G., Bontempi, B., Chavez-Noriega, L., Menzaghi, F., Rao, T. S., Reid, R., Sacaan, A. I., Suto, C., Washburn, M., Lloyd, G. K., McDonald, I. A., *J. Med. Chem.* 1999, 42, 1684-1686; and DeVita, R. J., Goulet, M. T., Wyvratt, M. J., Fisher, M. H., Lo, J-L, Yang, Y. T., Cheng, K., Smith, R. G., *Bioorg. Med. Chem. Lett.* 1999, 9, 2621-2624.

Scheme 1a provides an example of such conventional synthetic methodology that starts with a chiral compound and relies on four steps to generate compound (Ia).

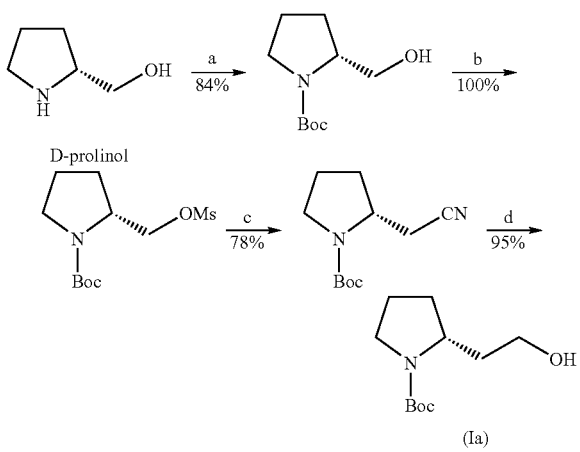

SCHEME 1a

With respect to Scheme 1a, a compound of formula (Ia) is prepared from a chiral starting material (D-prolinol). The reference letters a-d depicted with the reaction steps in the same scheme are given with the following meanings: (a)

BOC₂O, THF/H₂O, K₂CO₃; (b) CH₃SO₂Cl, Et₃N, CH₂Cl₂; (c) NaCN, DMF; and (d) hydrolysis to a methyl ester and then reduction in the presence of LiAlH₄, Et₂O, as in the last step of Scheme 1b.

Scheme 1b provides another example of conventional synthetic methodology that starts with a chiral compound and relies on a plurality of steps to generate compound (Ia).

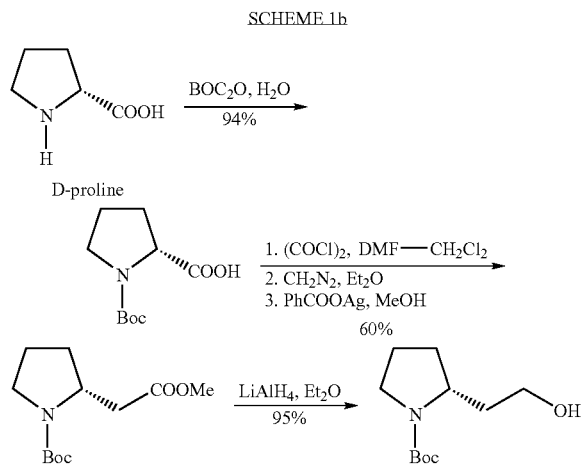

SCHEME 1b

With respect to Scheme 1b, a compound of formula (Ia) is prepared from a chiral starting material (D-proline) according to the synthetic steps shown therein.

Figures given as percentages in reaction steps refer to yields in the respective steps. For example, the figure "95%" in Scheme 1b means that the last step in such Scheme produces the final product with a yield of 95% (which unless indicated otherwise is calculated in terms of mass with respect to the maximum theoretically possible quantity of product that could be obtained in that step).

It is desirable to prepare chiral alkylated derivatives of nitrogen-containing heterocycles, such as compound of formula (Ia), from readily available inexpensive starting materials. Low complexity starting materials, such as achiral compounds are typically desirable, for they are generally more readily available and/or less expensive than chiral counterparts. It is also desirable that the, synthetic methods be suitable for large-scale synthesis, and that they involve a small number of steps, preferably one step. Where chirality is involved, it is also desirable to develop a synthesis that is as highly stereoselective as possible, so that a high ee of the product reduces, or even eliminates, the need for subsequent isolation and purifiction steps. In addition, desirable synthetic methods should preferably generate the chiral alkylated derivatives of nitrogen-containing heterocycles, such as compound of formula (Ia), in high yield.

Embodiments of the present invention provide desirable features such as those refered to above. Furthermore, embodiments of this invention provide synthetic methods for chiral alkylated derivatives of nitrogen-containing heterocycles, such as chiral hydroxy-alkyl derivatives of nitrogen-containing heterocycles, including a compound of formula (Ia), that solve synthetic problems that are not known to have been solved, or even addressed, by conventional methodologies.

For example, (−)-sparteine-mediated asymmetric deprotonative lithiation has been used to generate chiral carbanions. See, for example, Hoppe, D., Hense, T., Angew. Chem. Int. Ed. Engl. 1997, 36, 2282-2316; Beak, P., Basu, A., Gallagher, D. J., Park, Y. S., Thayumanavan, S., Acc. Chem. Res. 1996, 29, 552-560; Johnson, T. A., Jang, D. O., Slafer, B. W., Curtis, M. D., Beak, P., J. Am. Chem. Soc. 2002, 124,11689-11698; Laumer, J. M., Kim, D. D., Beak, P., J. Org. Chem. 2002, 67, 6797-6804; Lim, S. H., Beak, P., Org. Lett. 2002, 4, 2657-2660; Johnson, T. A., Curtis, M. D., Beak, P., Org. Lett. 2002, 4, 2747-2749; Christoph, G., Hoppe, D., Org. Lett. 2002, 4, 2189-2192; Arrasate, S., Lete, E., Sotomayor, N., Tetrahedron: Asymmetry 2002, 13, 311-316; and Metallinos, C., Snieckus, V., Org. Lett. 2002, 4, 1935-1938. Furthermore, a reportedly readily available (+)-sparteine surrogate has been introduced for its use in place of (+)-sparteine, which is not commercially available. See, for example, Dearden, M. J., Firkin, C. R., Hermet, J. R., O'Brien, P., J. Am. Chem. Soc. 2002, 124,11870-11871.

Conventional methods, however, rely on strong electrophiles, such as TMSCl, Bu₃SnCl, Me₂SO₄, aldehydes, and ketones. See, for example, Beak, P., Kerrick, S. T., Wu, S. D., Chu, J. X., J. Am. Chem. Soc. 1994, 116, 3231-3239. In contrast, methodology according to this invention uses weak electrophiles, such as strained cyclic ethers. Conventional methodology does not address the suitability of weak electrophiles. In addition, conventional methodology does not address the conditions under which such electrophiles could be used effectively. Even more specifically, conventional methodology does not address the issue of whether weak electrophiles could be used at all. Furthermore, conventional methodology does not appear to suggest the results of using such eletrophiles, even if such use could be effectively implemented. Moreover, the reported use (see, for example, Dearden, M. J., Firkin, C. R., Hermet, J. R., O'Brien, P., J. Am. Chem. Soc. 2002, 124, 11870-11871) of an epoxide in an intramolecular example wherein the epoxide opening is not activated by complexation with a Lewis acid, does not teach the use, in the presence of a Lewis acid, of a strained cyclic ether in an intermolecular process as an electrophilic partner of a sparteine/organometallic complex. Although Lewis acids have been reported as being capable of activating an epoxide for nucleophilic attack, and alkyl lithium reagents have been reported to react with epoxides that have been activated with BF₃.Et₂O (see, for example, Yamaguchi, N., Hirao, I., Tetrahedron Lett. 1983, 24, 391-394; Bachi, M. D., Bosch, E., Tetrahedron Lett. 1986, 27, 641-644), such reported activations do not address the chiral synthesis with sparteine-organometallic complexes and Lewis acid-activated strained cyclic ethers from achiral nitrogen-containing heterocycles.

In contrast with the conventional methodologies, embodiments of this invention provide efficient one-step methods for synthesizing versatile precursors of many bioactive molecules in high efficiency and enantioselectrivity by nucleophilic ring opening of a strained cyclic ether by a chiral N-heterocycle-metal-diamine complex, promoted by a Lewis acid.

References cited throughout the specification are incorporated herein by reference.

SUMMARY OF THE INVENTION

Embodiments of this invention feature chiral diamine-mediated asymmetric alkylation with a strained cyclic ether in the presence of a Lewis acid. Embodiments of this invention permit a high yield, and/or high ee, and/or one-step synthesis of chiral alkylated derivatives of nitrogen-containing heterocycles, such as chiral hydroxy-alkyl derivatives of nitrogen-containing heterocycles, including a compound of formula (Ia).

The invention features methods for making a chiral alkylated derivative of a nitrogen-containing heterocycle, such as a chiral hydroxy-alkyl derivative of a nitrogen-containing heterocycle, including but not limited to a compound of formula (Ia), comprising: incorporating into a medium with an α-substitutable-N-heterocycle at least an organometallic compound, a chiral diamine, a strained cyclic ether, and a Lewis acid.

Embodiments of methods for making a chiral alkylated derivative of a nitrogen-containing heterocycle, such as a chiral hydroxy-alkyl derivative of a nitrogen-containing heterocycle, including but not limited to a compound of formula (Ia), comprise embodiments wherein the chiral diamine, the organometallic compound, and the α-substitutable-N-heterocycle form in said medium a N-heterocycle-metal-chiral diamine complex, and said medium is temperature-controlled, so that the complex is thermally stable in such medium.

Embodiments of methods for making a chiral alkylated derivative of a nitrogen-containing heterocycle, such as a chiral hydroxy-alkyl derivative of a nitrogen-containing heterocycle, including but not limited to a compound of formula (Ia), comprise embodiments wherein the medium is temperature-controlled, so that it is at a temperature in the range from about −75° C. to about −100° C.

Embodiments of methods for making a chiral alkylated derivative of a nitrogen-containing heterocycle, such as a chiral hydroxy-alkyl derivative of a nitrogen-containing heterocycle, including but not limited to a compound of formula (Ia), comprise embodiments wherein the medium initially contains the α-substitutable-N-heterocycle and the chiral diamine, and wherein the incorporating proceeds by incorporating first the organometallic compound, followed by incorporating the strained ether and the Lewis acid. In some embodiments, the strained cyclic ether is incorporated before the Lewis acid is incorporated.

DETAILED DESCRIPTION

The present invention is directed to methods of making chiral alkylated derivatives of nitrogen-containing heterocycles, including but not limited to chiral hydroxy-alkyl derivatives of nitrogen-containing heterocycles, such as a compound of formula (Ia). Nitrogen-containing heterocycles in the context of this invention are concisely referred to herein with the term "α-substitutable-N-heterocycle".

The following terms are defined below, and by their usage throughout the disclosure.

The terms "strained cyclic ether" and morphologic variations thereof are meant to refer to compounds in which an oxygen member is attached directly to two adjacent or non-adjacent carbon members of a carbon chain or ring system and where the cycle (ring) that contains the ether moiety is strained. It has been found in the context of this invention that such ring strain should be not less than about 85 kJ mol$^{-1}$, preferably at least about 100 kJ mol$^{-1}$, and more preferably at least about 105 kJ mol$^{-1}$. For example, the ring strain energy of oxetane is considered to be about 107 kJ mol$^{-1}$, and the ring strain energy of oxirane is considered to be about 114 kJ mol$^{-1}$.

Strained cyclic ethers therefore comprise epoxy compounds, including epoxides (cyclic ethers derived from oxirane) that have such ring strain characteristics, and derivatives thereof. Examples of strained cyclic ethers are oxirane (ethylene oxide), oxirane derivatives, such as oxirane with at least one substituent, oxetane, oxetane derivatives, such as oxetane with at least one substituent, oxirene derivatives, such as oxirene with at least one substituent, 9,10-epoxy-9,10-dihydroanthracene, 1,2-epoxypropane, 2,3-epoxybutane and generally epoxides, including spiro oxirane derivatives, such as 1-oxa-spiro[2.2]pentane. Oxa-bicyclo-alkanes and derivatives thereof, and oxa-bicyclo-alkenes and derivatives thereof, provide additional examples of strained cyclic ethers, and illustrative embodiments of such additional examples are 2-oxa-bicyclo[1.1.0]butane, 5-oxa-bicyclo[2.1.0]pentane, 6-oxa-bicyclo[3.1.0]hexane, 7-oxa-bicyclo[4.1.0]heptane, 8-oxa-bicyclo[5.1.0]octane, 9-oxa-bicyclo[6.1.0]nonane, 2-oxa-bicyclo[1.1.1]pentane, 2-oxa-tricyclo[1.1.1.0$^{1,3}$]pentane, 5-oxa-bicyclo[2.1.1]hexane, 5-oxa-tricyclo[2.1.1.0$^{1,4}$]hexane, 8-oxa-tricyclo[3.2.1.0$^{1,5}$]octane, 7-oxa-bicyclo[2.2.1]heptane, 7-oxa-tricyclo[2.2.1.0$^{1,4}$]heptane, 2-oxa-bicyclo[2.2.2]oct-1(7)-ene, 2-oxa-bicyclo[2.2.2]oct-4(8)-ene, 2-oxa-tricyclo[2.2.2.0$^{1,4}$]octane, 11-oxa-bicyclo[4.4.1]undec-1(10)-ene, 2-oxa-tricyclo[3.3.1.1$^{3,7}$]dec-1(9)-ene, and cyclanic structures, such as 3-oxaquadricyclane, and oxaquadricyclanes. Derivatives in this context include at least one of substitutions, unsaturations, and spiro structures. Strained cyclic ethers according to this invention include ethers with skeletal structures such as the following:

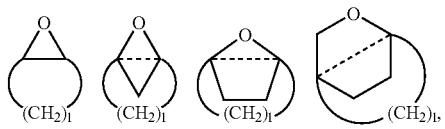

and analogous skeletal structures with insaturation(s), and/or substitution(s), where/≧0, and derivatives thereof.

Whether a certain structure has the strain characteristics described herein is something that can be determined in light of the teachings provided herein and available reference material on the strain of carbocycles and heterocycles. In this regard, see for example, F. A. Carey and R. J. Sundberg, Advanced Organic Chemistry, part A, 3$^{rd}$ ed. (1993), pp. 157-163; A. S. Pell and G. Pilcher, Trans. Faraday Soc. 61, 71 (1965); and http://www.chm.bris.ac.uk/aldergroup/level3/ch300123.htm.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on.

"Alkenyl" includes straight chain and branched hydrocarbon radicals as above with at least one carbon-carbon double bond (sp$^2$). Unless indicated otherwise by the prefix that indicates the number of carbon members, alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on.

"Alkynyl" includes straight chain and branched hydrocarbon radicals as above with at least one carbon-carbon triple bond (sp). Unless indicated otherwise by the prefix that indicates the number of carbon members, alkynyls include ethynyl, propynyls, butynyls, and pentynyls. Hydrocarbon radicals having a mixture of double bonds and triple bonds, such as 2-penten-4-ynyl, are grouped as akynyls herein.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and SO$_2$.

Unless indicated otherwise by the prefix that indicates the number of carbon members, "cycloalkyl" includes cyclopropyl, cyclobutyl, cyclopentyl, cyclohexyl, cycloheptyl, cyclooctyl, and so on.

Unless indicated otherwise by the prefix that indicates the number of members in the cyclic structure, "heterocyclyl" or "heterocycle" is a 3- to 8-member aromatic, saturated, or partially saturated single or fused ring system that comprises carbon atoms wherein the heteroatoms are selected, unless otherwise indicated, from N, O, and S. Examples of heterocyclyls include thiazolyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imidazolidinyl, imidazolinyl, pyrazolidinyl, pyrazolinyl, piperidyl, piperazinyl, cyclohexylimino, cycloheptylimino, indolinyl, and morpholinyl. Examples of nitrogen-containing heterocycles, and in particular examples of α-substitutable-N-heterocycles are aziridine, azetidine, pyrrolidine, piperidine, hexahydroazepine, azocane, imidazolidine, pyrazolidine, hexahydropyridazine, hexahydropyrimidine, piperazine, and forms of such nitrogen-containing heterocycles that have at least one protected amino group.

Examples of organometallic compounds are organo-alkali metal compounds, such as alkyl-alkali metal compounds. An organolithium compound is an example of an organo-alkali metal compound. An alkyllithium compound is an example of an alkyl-alkali metal compound. Secondary butyllithium (s-BuLi) is an example of an alkyllithium compound.

"Halo" includes fluoro, chloro, bromo, and iodo, and is preferably fluoro or chloro.

As in standard chemical nomenclature, the group phenyl is herein referred to as "phenyl" or as "Ph".

(−)-Sparteine is the known compound [7S-(7α,7aα,14α, 14aβ)]-dodecahydro-7,14-methano-2H,6H-dipyrido[1,2-a: 1',2'-e]-[1,5]diazocine. See, for example, The Merck Index, 13$^{th}$ ed. (2001), entry #8810. The same entry refers in addition to the sulfate pentahydrate and to l-α-isosparteine. See id., entry #8810, pp. 1557-58.

Terms such as "stereoselective", "stereoselectivity", and morphologic variations thereof refer to the production of stereoisomeric products in unequal amounts. As conventionally used, enantiomeric excess (often abbreviated as "ee") means herein $|F_{(+)}-F_{(-)}|$, where $F_{(+)}$ denotes mole fraction (or mass fraction) of enantiomer (+), $F_{(-)}$ denotes mole fraction (or mass fraction) of enantiomer (−), and $F_{(+)}+F_{(-)}=1$. When given as a percentage, enantiomeric excess is $100.|F_{(+)}-F_{(-)}|$.

Terms such as "racemic", "racemate", and morphologic variations thereof apply as used herein to mixtures in which the enantiomers are present in equimolar amounts (ee=0) and such mixtures do not exhibit optical activity.

It is understood that substitutions and combinations of substitutions recited herein, whether stated explicitly or not, refer to substitutions that are consistent with the valency of the member being substituted. For example, a substitution applied to a carbon member refers to the tetravalency of C; it refers to the trivalency of N when applied to a nitrogen member; and it refers to the tetravalency of a nitrogen member that is conventionally characterized with a positive electric charge. Valence allowed options are part of the ordinary skill in the art.

Embodiments of methods for making a chiral alkylated derivative of a nitrogen-containing heterocycle, such as a chiral hydroxy-alkyl derivative of a nitrogen-containing heterocycle, including but not limited to a compound of formula (Ia), include methods wherein at least one of the following is satisfied:

said α-substitutable-N-heterocycle is one of aziridine, azetidine, pyrrolidine, piperidine, hexahydroazepine, azocane, and mixtures thereof; wherein each of said α-substitutable-N-heterocycle has its >NH member protected;

said α-substitutable-N-heterocycle is one of imidazolidine, pyrazolidine, hexahydropyridazine, hexahydropyrimidine, piperazineaziridine, and mixtures thereof; wherein each of said α-substitutable-N-heterocycle has at least one of its >NH members protected;

said α-substitutable-N-heterocycle is one of 1-Boc-aziridine, 1-Boc-azetidine, 1-Boc-pyrrolidine, 1-Boc-piperidine, 1-Boc-hexahydroazepine, and 1-Boc-azocane, and mixtures thereof;

said α-substitutable-N-heterocycle is 1-Boc-pyrrolidine;

said strained cyclic ether is an epoxide, and said epoxide is one of oxirane, oxirene, 1,2-epoxypropane, and 2,3-epoxybutane;

said strained cyclic ether is 9,10-epoxy-9,10-dihydroanthracene;

said strained cyclic ether is one of 1-oxa-spiro[2.2]pentane; 2-oxa-bicyclo[1.1.0]butane, 5-oxa-bicyclo[2.1.0]pentane, 6-oxa-bicyclo[3.1.0]hexane, 7-oxa-bicyclo[4.1.0]heptane, 8-oxa-bicyclo[5.1.0]octane, 9-oxa-bicyclo[6.1.0]nonane, 2-oxa-bicyclo[1.1.1]pentane, 2-oxa-tricyclo[1.1.1.0$^{1,3}$]pentane, 5-oxa-bicyclo[2.1.1]hexane, 5-oxa-tricyclo[2.1.1.0$^{1,4}$]hexane, 8-oxa-tricyclo[3.2.1.0$^{1,5}$]octane, 7-oxa-bicyclo[2.2.1]heptane, 7-oxa-tricyclo[2.2.1.0$^{1,4}$]heptane, 2-oxa-bicyclo[2.2.2]oct-1(7)-ene, 2-oxa-bicyclo[2.2.2] oct-4(8)-ene, 2-oxa-tricyclo[2.2.2.0$^{1,4}$]octane, 11-oxa-bicyclo[4.4.1]undec-1(10)-ene, 2-oxa-tricyclo[3.3.1.1$^{3,7}$]dec-1(9)-ene, and 3-oxaquadricyclane;

said strained cyclic ether is one of oxirane, oxirene, and oxetane;

said organometallic compound is organolithium;

said organometallic compound is organolithium, and said organolithium is alkyllithium;

said organometallic compound is s-BuLi;

said Lewis acid is $BF_3$;

said Lewis acid is $BF_3$ and said Lewis acid is provided as $BF_3.Et_2O$;

said temperature is in the range from about −75° C. to about −100° C.;

said temperature is in the range from about −78° C. to about −100° C.;

said temperature is in the range from about −80° C. to about −100° C.;

said temperature is in the range from about −75° C. to about −90° C.;

said temperature is in the range from about −75° C. to about −80° C.;

said temperature is about −78° C.;

said medium is provided by an ether-based solvent;

said medium is provided by one of $Et_2O$, TBME, dimethyl ether, dipropyl ether, and mixtures thereof;

said medium is provided by the solvent $Et_2O$;

said incorporating comprises incorporating first said strained cyclic ether, and subsequently adding a $BF_3$-containing Lewis acid;

said incorporating comprises incorporating first said strained cyclic ether, and subsequently adding $BF_3.Et_2O$;

said incorporating comprises incorporating ethylene oxide as said strained cyclic ether, and subsequently adding said Lewis acid;

said incorporating comprises incorporating first ethylene oxide as said strained cyclic ether, and adding subsequently BF$_3$.Et$_2$O;

said chiral diamine comprises at least one of (−)-sparteine, (+)-sparteine, and (+)-sparteine surrogate;

said α-substitutable-N-heterocycle has an amino group that is protected with a protection group wherein said protection group has at least one of an alkanoyl group, an alkoxycarbonyl group, an aroyl group, a phthaloyl group, an arylmethoxycarbonyl group, and a pivaloyl group;

said α-substitutable-N-heterocycle comprises 1-Boc-pyrrolidine, said organometallic compound comprises s-BuLi, said chiral diamine comprises (−)-sparteine, said strained cyclic ether comprises ethylene oxide, said Lewis acid comprises BF$_3$.Et$_2$O, and said medium comprises Et$_2$O;

said α-substitutable-N-heterocycle is 1-Boc-pyrrolidine, said organometallic compound is s-BuLi, said chiral diamine is (−)-sparteine, said strained cyclic ether is ethylene oxide, said Lewis acid is BF$_3$.Et$_2$O, and said medium is provided by the solvent Et$_2$O.

Terms such as "reacting", "forming", and related terms, applied to a chemical entity herein refer to any one of: (a) the chemical entity as such, and (b) the chemical entity in the form in which such entity is present in the reaction medium. Analogously, to name a chemical entity in the context of an operation or reaction step, or as being in a medium, refers herein to any one of: (a) the entity as such, and (b) the entity in the form in which such entity is present in the medium. For example, the expression "A and B in a reaction medium . . . " refers to entities "A" and "B" as they are in such medium. The terms "reagent A is available commercially" refers to the entity "A" as such entity in the form in which it can be obtained from commercial sources.

Starting materials for methods according to this invention may be obtained from commercial sources or synthesized by methods known to one skilled in the art. Alternatively, it may be necessary to employ, in the place of the ultimately desired substituent, a suitable group, which may be carried through the reaction scheme and replaced as appropriate with the desired substituent. Any product containing a chiral center may be separated into its enantiomers by conventional techniques.

Some embodiments of processes illustrated herein include, as additional steps and when chemically meaningful, one or more steps such as hydrolysis, halogenation, homologation, protection, and deprotection. These additional steps, including but not limited to those referred to herein, can be implemented in light of the teachings provided herein and the ordinary skill in the art.

To obtain the various compounds described herein and equivalents thereof, starting materials may be employed that carry the ultimately desired substituents through the reaction scheme with or without protection as appropriate. Alternatively, it may be necessary to employ, in the place of the ultimately desired substituent, a suitable group that may be carried through the reaction scheme and replaced as appropriate with the desired substituent.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J.F.W. McOmie, Plenum Press, 1973; and T.W.Greene & P.G.M. Wuts, "Protective Groups in Organic Synthesis", 3rd ed., John Wiley & Sons, 1999; further examples of protecting groups are well known in organic synthesis and the peptide art, and are described by M. Bodanzsky, *Principles of Peptide Synthesis,* 1st and 2nd revised ed., Springer-Verlag, New York, 1984 and 1993; Stewart and Young, Solid *Phase Peptide Synthesis,* 2nd ed., Pierce Chemical Co, Rockford, Ill. 1984; L. Fieser and M. Fieser, *Fieser and Fieser's Reagents for Organic Synthesis,* John Wiley and Sons (1994); L. Paquette, ed. *Encyclopedia of Reagents for Organic Synthesis,* John Wiley and Sons (1995). Amino protecting groups are also given in, e.g., WO 98/07685. The protecting groups may be removed at a convenient subsequent stage using methods known from the art. One or more than one protecting group may often be used in a protection/deprotection operation. The choice typically intends to provide a protected group that will be stable under the conditions of subsequent reactions, and that can be removed at an appropriate step without disrupting the rest of the compound.

It is understood, for example, that nitrogen-containing heterocycles that exhibit a >NH group can be prepared in the corresponding forms with such group being protected. By way of illustration, but not as a limitation, amine protection/deprotection can be achieved by incorporating/removing groups such as the following: acyl groups that can be used to protect an amino, or alkylamino, group include an alkanoyl group, such as acetyl, an alkoxycarbonyl group, such as methoxycarbonyl, ethoxycarbonyl, and t-butoxycarbonyl, and an aroyl group, such as benzoyl.

As known in the conventional practice of these protection reactions, deprotection conditions vary with the protecting group. Groups such as an alkanoyl, alkoxycarbonyl, or aroyl may be removed, for example, by hydrolysis with a suitable base, such as an alkali metal hydroxide. Other groups, such as a t-butoxycarbonyl group, may be removed by, for example, treatment with an acid, such as hydrochloric, sulfuric, phosphoric, or trifluoroacetic.

Arylmethoxycarbonyl groups, such as benzyloxycarbonyl, may be removed by, for example, hydrogenation in the presence of a catalyst, such as palladium-on-carbon, or by treatment with a Lewis acid, such as boron tris(trifluoroacetate). A phthaloyl group protecting a primary amino group may be removed by, for example, treatment with an alkylamine, such as dimethylaminopropylamine, or with hydrazine.

It is understood, for example, that nitrogen-containing heterocycles according to this invention that exhibit a >NH group can be obtained in the corresponding forms with such group in a protected form.

SCHEME 2

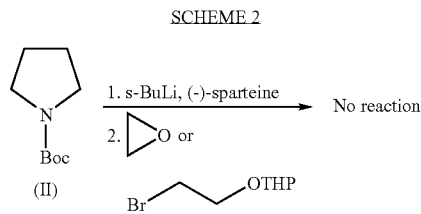

Referring to Scheme 2, there are disclosed the following notes and additions. (−)-Sparteine-mediated asymmetric alkylation of an achiral starting material with an epoxide or an equivalent thereof was attempted under conventional s-BuLi-(−)-sparteine complex conditions (see, for example, Beak, P., Kerrick, S. T., Wu, S. D., Chu, J. X., *J. Am. Chem. Soc.* 1994, 116, 3231-3239). In some of these attempts, ethylene oxide was used as electrophile. O-THP-protected 2-bromoethanol was used as electrophile in other attempts. Et$_2$O was used as solvent and the experiments were conducted at temperatures of about −78° C. for about 4 h. However, no detectable reaction was observed in any such attempts under conventional conditions, and the starting achiral material was recovered essentially unreacted, as indicated in Scheme 2.

Additional conventional conditions (not shown in Scheme.2) were also tried, but no detectable reaction was observed under such conditions. Such additional conventional conditions included those under which an organolithium-sparteine complex can reportedly be transmetallated to an organocopper derivative (see, for example, Kieter, R. K., Sharma, R. R., Tetrahedron Lett. 1997, 38, 5937-5940; and Kieter, R. K., Lu, K., Velu, S. E., J. Org. Chem. 2000, 65, 8715-8724), and to an organomagnesium derivative (see, for example, Kise, N., Urai, T., Yoshida, J-I, Tetrahedron:Asymmetry 1998, 9, 3125-3128).

Novel processes and reaction conditions had to be developed in the context of this invention to achieve the synthesis of chiral alkylated derivatives of nitrogen-containing heterocycles from an achiral nitrogen-containing heterocycle as described herein.

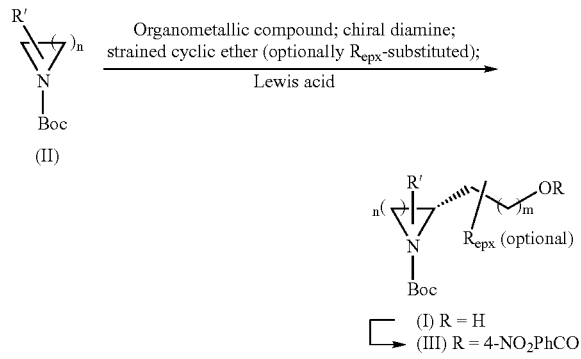

Referring to Scheme 3, there are disclosed the following notes and additions. The starting materials are commercially available or their synthesis is within the skill of the art. Compound of formula (II) can be prepared from the corresponding amine by a conventional protection reaction with di-tert-butyl dicarbonate. An example of a precursor to form compound of formula (II) is the amine

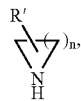

an α-substitutable-N-heterocycle. Examples of compounds of formula (II) include nitrogen-containing heterocycles with at least one protected N-member, such as the protected forms of aziridine, azetidine, pyrrolidine, piperidine, hexahydroazepine, azocane, imidazolidine, pyrazolidine, hexahydropyridazine, hexahydropyrimidine, and piperazine. One of the carbon members that is in an α position to the (protected) nitrogen member in a (protected) α-substitutable-N-heterocycle is a saturated carbon with not more than one substituent. As these examples illustrate, any of such nitrogen containing heterocycles can optionally be R' substituted provided that at least one carbon member that is in an α position to the protected nitrogen member has the characteristics described herein. Whether protected or not, embodiments of α-substitutable-N-heterocycles according to this invention are nitrogen-containing saturated heterocycles which can be deprotonated at the α carbon with a strong base. Examples of these embodiments include nitrogen-containing saturated heterocycles which can be lithiated at the a carbon by deprotonation with a strong base, such as secondary butyllithium.

Because protection of an >NH member in such α-substitutable-N-heterocycles can be accomplished by methods known by those of ordinay skill in the art, and the choice of the protecting groups can be made in light of the teachings provided herein, the term "α-substitutable-N-heterocycle" herein refers, unless more specifically characterized, to any one of (a) a nitrogen-containing heterocycle as characterized herein, and (b) a protected form of such nitrogen-containing hererocycle.

Embodiments of this invention are not limited to any specific mechanism. It is believed that at least in some embodiments of this invention, compound of formula (I) is formed by generating an organometallic-chiral diamine complex, such as an organometallic-(−)-sparteine complex, and exposing a compound of formula (II) to such complex, an strained cyclic ether, and a Lewis acid. R is H for compound of formula (I) in Scheme 3. When referring to the complex formed with a metal, a chiral diamine, and a compound of formula (II), the term "N-heterocycle-metal-chiral diamine complex" is used herein. Examples of such complexes are N-heterocycle-metal-(−)-sparteine complex, N-heterocycle-metal-(+)-sparteine surrogate complex, and N-heterocycle-metal-(+)-sparteine complex. Examples of chiral diamine compounds are given by (−)-sparteine, (+)-sparteine, and (+)-sparteine surrogate, which have the structures:

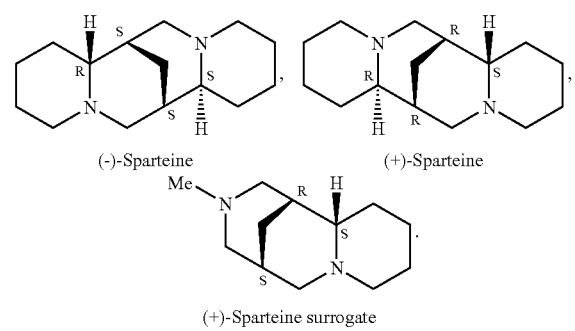

One of ordinary skill in the art will be able to ascertain when the use of related compounds, such as a salt and/or a stereoisomer of the various forms of chiral diamine, such as sparteine, can be used in this context. Some of such related compounds will be appropriately transformed to be used in embodiments of this invention. For example, a salt would be converted to a free base. The sulfate pentahydrate is an example of a salt. L-α-Isosparteine is an example of a stereo isomer.

Epoxide synthesis can be achieved by known methods, such as with a peroxyacid, optionally substituted, for example with magnesium monoperoxyphthalic acid (MMPP), and an optionally substituted alkene. For example, the reaction of a cycloalkene with a peroxyacid yields a 1,2-epoxycycloalkane. Epoxide synthesis can also be accomplished by a basic treatment of an optionally substituted halohydrin.

Examples of the N-heterocycle-metal-chiral diamine complexes are given by a N-heterocycle-alkali metal-(−)-sparteine complex, preferably a N-heterocyclyllithium-(−)-sparteine complex.

As will be appreciated by one of ordinary skill in the art, the strained cyclic ether in Scheme 3 is suitably chosen, so that it incorporates upon alkylation a desired functionality(ies) and/or substitution(s) in the alkyl chain that is attached to the cyclic structure of the starting achiral material. For example, a strained cyclic ether such as oxirane (ethylene oxide), oxirene and oxetane is used when the inserted side chain is desired to be straight and have two (m=1) when at least one of oxirane and oxirene is used, or three (m=2), when oxetane is used, carbon members. It is understood that m can have other values provided that m be a non-zero positive integer. Longer chains (i.e., greater m values) can be achieved by implementing known homologation chemistry. An epoxide such as 1,2-epoxypropane or 2,3-epoxybutane is preferably used when the inserted side chain is desired to be branched and have three or four carbon members. A strained cyclic ether with a cyclic member, such as 9,10-epoxy-9,10-dihydroanthracene, can be used when the inserted side chain is desired to have cyclic members, including saturated/unsaturated cyclic members. A strained cyclic ether with a cyclic member and suitable substitution, such as suitably substituted 9,10-epoxy-9,10-dihydroanthracene, can be used when the inserted side chain is desired to have suitably substituted cyclic members, including suitably substituted saturated/unsaturated cyclic members. One of ordinary skill in the art would be able to make the appropriate selections according to the teachings provided herein, including the selections of the desired substituents in the introduced side chain that are chemically compatible with the reaction conditions according to the present invention. Examples of optional subsituents in the strained cyclic ether include at least one of alkyl, alkenyl, akynyl, alkoxy, aminoalkyl, thioalkyl, cycloalkyl, heterocyclyl, halo, and phenyl. Whether there is one or a plurality of such substituents, they are collectively referred to herein as $R_{epx}$.

An achiral starting material, such as compound of formula (II), can be provided in the form of compound of formula (II) or as the corresponding unprotected nitrogen-containing heterocycle. In the latter case, and during the processes for preparation of a compound of formula (II), the nitrogen member in the heterocycle is protected, preferably with Boc, as shown in Scheme 3. Another example of a protecting group is a pivaloyl group, and further examples are given herein in reference to protection/deprotection of the >NH member. Preferable protecting groups are such that they exhibit a carbonyl group as the attachment group to the nitrogen member that they protect. Furthermore, preferable protecting groups exhibit a carbonyl group as the attachment group to the nitrogen member that they protect, and such carbonyl group is located between the nitrogen member being protected and a moiety in the protecting group that does not have easily removable protons. A person of ordinary skill in the art would be able to, in light of the teachings provided herein, select a suitable protecting group that does not adversely affect the stability of the nitrogen-containing heterocycle alkali metal chiral diamine complex under reaction conditions.

The methods claimed herein are not limited to any single mechanism. It is believed that at least in some embodiments of the methodologies of this invention a chiral complex involving a nitrogen-containing heterocycle, the nitrogen protecting group in such heterocycle, and a metal-chiral diamine complex is formed. In light of work developed in the context of this invention, such complex is predicted to have the following structure:

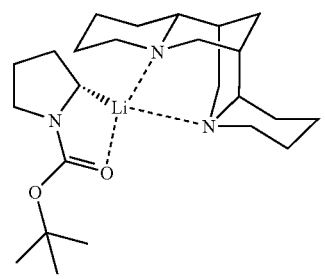

Complex structure (CS1)

Complex structure (CS1) shows, as an example and not by way of limitation, a possible embodiment of a N-heterocycle-metal-chiral diamine complex, where the protection of the nitrogen member in the heterocycle is illustrated by Boc protection, where such N-heterocycle is exemplified by pyrrolidine, where the chiral diamine is illustrated by (−)-sparteine, and where the metal is illustrated by Li.

R' in Scheme 3 stands collectively for any number of optional substituents in a nitrogen-containing heterocycle, such as compound of formula (II). Compound of formula (II) is unsubstituted in some embodiments of this invention. In other embodiments, R' denotes one or a plurality of substituents in the heterocycle. When R' denotes a plurality of substituents, such substituents are identical in some embodiments, whereas they are different in other embodiments. A person of ordinary skill in the art would be able to, in light of the teachings provided herein, select a suitable substituent, both in number and chemical identity, so that such substituents, if any, do not adversely affect, and are not adversely affected by, the reaction conditions and/or other chemical species in embodiments of this invention. The number and/or chemical identity of each substituent(s), if any, are chosen in light of the characteristics of the product of formula (I) that is desired. Examples of R' include at least one of alkyl, alkenyl, akynyl, alkoxy, thioalkyl, cycloalkyl, heterocyclyl, and phenyl.

An "achiral" starting material, such as an achiral compound of formula (II), refers herein to the starting material for a reaction according to Scheme 3 such that the member to be alkylated is not a stereogenic center, although the starting material could be chiral at other molecular centers. It is understood that the starting material has, in some embodiments, chirality because of, for example, the characteristics of at least one stereogenic center that is not the member to be alkylated, such as a stereogenic center at an R' substituent. Such starting material is referred to herein as "achiral", because chirality is generated by embodiments of methodologies according to this invention at the member being alkylated. Analogously, the term "chiral" refers, unless specified otherwise, to the chiral property of the member in the nitrogen-containing heterocycle that is alkylated.

It is understood that the organometallic-chiral diamine complex referred to in Scheme 3 is meant to refer to specific complexes of an organometallic with a chiral diamine, such as (−)-sparteine, and also to any other complex that is equivalent to the complex referred to.

Embodiments of the reaction shown in Scheme 3 preferably proceed in the same medium, also referred to as the reaction medium, thus providing a one step transformation that generates the desired compound of formula (I). This compound can be further transformed according to known processes. For example additional steps can introduce substituents, and/or utilize the reactivity of the hydroxy group for further reactions.

In preferred embodiments, the transformation shown in Scheme 3 proceeds by adding an organometallic compound to a medium that contains a compund of formula (II) and a chiral diamine, such as (−)-sparteine. Embodiments of such organometallic compounds are organo alkali metal compounds, preferably organolithium compounds, and more preferably alkyllithium compounds. Examples include s-BuLi and i-propyl-Li, with s-BuLi being more preferred. The strained cyclic ether and the Lewis acid are then added into the medium, preferably in a way such that the Lewis acid follows the addition of the strained cyclic ether. Progress of the reaction can be monitored by conventional techniques. Quenching, extraction, and isolation are also performed according to conventional methods.

Complex formation operations that are believed to lead to the formation of a N-heterocycle-metal-chiral diamine complex in some embodiments of this invention include incorporating a chiral diamine and an organometallic compound into a medium that contains an α-substitutable-N-heterocycle. Such complex formation operations exemplify embodiments of a step for forming a N-heterocycle-metal-chiral diamine complex.

Activation operations that are believed to lead to the activation of a strained cyclic ether for reacting with a nucleophilic member include incorporating into a medium a strained cyclic ether and a Lewis acid into such medium. Such activation operations exemplify embodiments of a step for activating a strained cyclic ether. These activation operations include those that are believed to lead to the activation of a strained cyclic ether for reacting with a nucleophilic member in a N-heterocycle-metal-chiral diamine complex by incorporating a strained cyclic ether and a Lewis acid into a medium that contains a N-heterocycle-metal-chiral diamine complex. Such activation operations exemplify embodiments of a step for activating a strained cyclic ether for reacting with a nucleophilic member in a N-heterocycle-metal-chiral diamine complex.

Cyclic ethers used in embodiments of this invention are exemplified by strained cyclic ethers described herein and equivalents thereof. The use of certain cyclic ethers might lead to steric or lower ring strain impediments that would require more drastic reaction conditions, such as higher temperature. It is understood that a person of ordinary skill will be able to, in light of the teachings provided herein, ascertain when a temperature is high enough, and therefore prohibitive, to disrupt the effective performance of the reactions described herein. Increasing the temperature to such high value or beyond would lead to a disruption of the reaction, thus leading to poor or undetectable yields. It is believed that such high temperature effects would be associated with a disruption of the stability of a N-heterocycle-metal-chiral diamine comlex.

It is known that certain Lewis acids can activate an epoxide. Absent the teachings provided herein, however, conventional methodologies do not appear to teach whether activation will take place in an environment in which the strongly basic diamine, for example sparteine, could compete with epoxide for the Lewis acid and compromise the configurational integrity of the chiral metal-diamine complex, or whether activation will take place in such environment with the cyclic ethers used in embodiments of this invention. Furthermore, conventional methodologies do not appear to teach that chirality will be maintained under such reaction conditions.

It is believed that at least in some embodiments of this invention the Lewis acid activates the strained cyclic ether thus forming a weak electrophile, which in turn readily reacts with a N-heterocycle-metal-chiral diamine complex at the α-carbon member of the nitrogen-containing heterocycle that is complexed with the alkali metal-chiral diamine complex. This α-carbon member is believed to be in the form of a nucleophile (alkali metallated carbanion, such as lithiated carbanion). Whereas this mechanism can explain embodiments of this invention, the processes according to this invention themselves are not constrained by or limited to specific mechanisms. As described herein, the processes according to this invention have provided surprising results that were not achieved under conventional conditions, and references to conventional methodologies do not appear to teach the processes according to this invention.

Embodiments of the present invention generated compounds of formula (I) with yields of about 83%. Embodiments of the present invention generated compounds of formula (I) with ee of about 82%.

The order in which reactants are "incorporated" (used herein as "added") into the medium differs in some embodiments of this invention from the preferred order described above. For example, the Lewis acid was added into the medium prior to the addition of the strained cyclic ether in some embodiments. Lower yields are generated by some of such embodiments in which the order of addition of the strained cyclic ether and Lewis acid differs from the preferred order described above.

At least one of the operations shown in Scheme 3, such as the addition of an organometallic compound and a chiral diamine, the additon of a strained cyclic ether, and the addition of a Lewis acid, is carried out at a temperature in the range from about −75° C. to about −100° C. Other temperature ranges are exemplified by temperatures in the range from about −78° C. to about −100° C.; in the range from about −80° C. to about −100° C.; in the range from about −75° C. to about −90° C.; in the range from about −75° C. to about −80° C.; and by a temperature that is about −78° C. The entire process shown in Scheme 3 is performed at a temperature or temperatures that is/are within such ranges in preferred embodiments of this invention. A temperature of about −78° C. is preferred for some embodiments of this invention. With this guidance, one of ordinary skill in the art should be able to modify the medium temperature accoding to the characteristics of the specifc solvent and/or reacting species in such medium.

It is believed that at least in some embodiments of this invention the preferred temperature should be chosen so that it provides thermal conditions in the reaction medium under which a N-heterocycle-alkali metal-chiral diamine complex, such as complex (CS1), is stable. These conditions are referred to as conditions under which such complex is thermally stable in such reaction medium. Whereas this stability characteristic can explain the preferred temperature for some embodiments of this invention, the processes according to this inventon themselves are not constrained by or limited to specific theories on the effects of thermal conditions on a N-heterocycle-alkali metal-chiral diamine complex stability. As described herein, the processes according to this invention have provided surprising results that were not achieved under conventional conditions; the conventional methodologies disclosed in the uncovered references do not appear to teach the processes according to this invention.

Examples of saturated heterocycles that can embody the nitrogen-containing cyclic framework shown in Scheme 3 include aziridine, azetidine, pyrrolidine, piperidine, hexahydroazepine, and azocane. Although only one nitrogen member is shown in the cyclic structures in Scheme 3, it is understood that embodiments of this invention are not limited to such feature. For example, nitrogen-containing heterocycles in other embodiments of this invention contain more than one nitrogen member, and examples of such cyclic structures include imidazolidine, pyrazolidine, hexahydro-pyridazine, hexahydro-pyrimidine, and piperazine, all of them with two nitrogen members, of which at least one that can be protected with, for example, Boc, as shown in Scheme 3, and additional protecting groups are preferably orthogonal to the asymmetric alkylation chemistry.

Furthermore, only the portion that has the nitrogen-containing heterocycle is shown in Scheme 3, but this is not intended as a limiting feature of embodiments of this invention. In some embodiments, this is the only cyclic structure in the compound of formula (II). In other embodiments, an additional cyclic structure in the form of at least one fused ring is also part of compounds of formula (II) within the scope of the present invention.

Examples of solvents that can provide the reaction medium in embodiments of this invention are ether-based solvents, such as $Et_2O$, TBME, dimethyl ether, dipropyl ether, and mixtures thereof. A preferred solvent is $Et_2O$.

The hydroxy group in embodiments of compounds of formula (I) can be further transformed. The formation of 1-Boc-2-[2-(4-nitro-benzoyloxy)-ethyl]-pyrrolidine, optionally substituted with $R_{epx}$, (a compound of formula (IIIa)), which in Scheme 3 is a compound of formula (III) with n=3, m=1, and R'=H therein, is an example of the result of one of such transformations.

Embodiments of this invention generate the chiral product with a yield of at least 60%, the yield in other embodiments is at least 70%, the yield in other embodiments is at least 80%, and in additional embodiments the yield is at least 90%. Embodiments of this invention generate the chiral product with an ee of at least 60%, the ee in other embodiments is at least 70%, the ee in further embodiments is at least 80%, and the ee in additional embodiments is at least 90%.

SCHEME 4

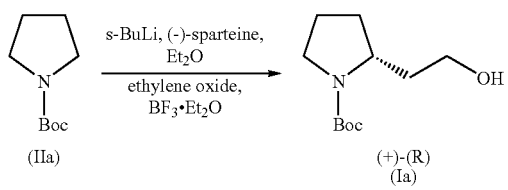

(IIa)   (+)-(R)
         (Ia)

Scheme 4 provides an example of an embodiment of the process shown in Scheme 3. In this particular embodiment, the chiral diamine is (−)-sparteine, the organometallic compound is an organolithium compound, and more concretely it is s-BuLi, the solvent is $Et_2O$, the strained cyclic ether is the epoxide ethylene oxide, the Lewis acid is $BF_3$, provided as $BF_3 \cdot Et_2O$, m=1, and n=3. A compound of formula (Ia) in Scheme 4 can be characterized as being the enantiomer (+)-(R) because it is obtained in an ee of at least 80%, and in some embodiments about 82%. A compound of formula (Ia) was obtained in embodiments of this invention with a yield of about 83% and ee of about 82%.

Examples of weak electrophiles in embodiments of this invention include strained cyclic ethers, whether provided as such or in an equivalent form, such as complexed with a Lewis acid. The terms "Lewis acid" as used herein refers to a Lewis-acid containing entity, so Lewis acid refers to any one of a Lewis acid, for example $BF_3$, and any equivalent form thereof, such as $BF_3 \cdot Et_2O$, that is used to incorporate the Lewis acid in the medium.

Where the processes for the preparation of the compounds according to the invention give rise to mixture of stereoisomers, these isomers may be separated by conventional techniques such as resolution, for example by formation of diastereomeric salts, kinetic resolution including variants thereof, such as dynamic resolution, preferential crystallization, biotransformation, enzymatic transformation, and preparative chromatography. The compounds may be prepared in non-racemic form, or individual enantiomers may be prepared either by enantioselective synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be separated using a chiral HPLC column.

It is understood that some compounds referred to herein have geometric isomeric centers, for example E- and Z-isomers, and/or have chiral centers at positions other than those explicitly shown herein. The present invention encompasses the methods of making all such optical, including stereoisomers and racemic mixtures, diastereomers, and geometric isomers, whether solvated or unsolvated, that can be implemented with the teachings provided herein. Additional modification steps that are implemented in the context of the processes of this invention and whose implementation renders the relevant compounds detectable by some analytical technique are also within the scope of this invention. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Another example of such compounds is an isotopically labeled compound, such as a deuterium and/or tritium labeled compound that may be used in reaction kinetic studies.

When the implementation of the teachings provided herein requires the formation in additional steps of pharmaceutically acceptable derivatives, representative acids and bases that may be used in the preparation of pharmaceutically acceptable salts include the following:

acids including acetic acid, 2,2-dichlorolactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid; stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

See, for example, S. M. Berge, et al., "Pharmaceutical Salts", *J. Pharm. Sci.* 1977, 66:1-19, which is incorporated herein by reference. Examples of suitable esters include $C_{1-7}$alkyl, $C_{5-7}$cycloalkyl, phenyl, substituted phenyl, and phenyl$C_{1-6}$alkyl-esters. Preferred esters include methyl esters.

Compounds that can be synthesized by embodiments of the present invention include prodrugs. In general, such prodrugs will be functional derivatives of the compounds that are readily convertible in vivo into the required compound. When methods according to this invention are to be implemented with prodrug derivative preparation, conventional procedures for the selection and preparation of suitable prodrug derivatives are described, for example, in "Design of Prodrugs", ed. H. Bundgaard, Elsevier, 1985.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

EXAMPLES

General Experimental Methods

NMR spectra were obtained on either a Bruker model DPX400 (400 MHz; 13C, 100 MHz) or DPX500 (500 MHz) spectrometer. The format of the $^1$H NMR data below is: chemical shift in ppm down field of the tetramethylsilane reference (multiplicity, coupling constant J in Hz, integration).

Mass spectra were obtained on an Agilent series 1100 MSD

Infrared Spectroscopy was performed on a Nicolet Avatar 360 FT-IR.

Elemental analyses were performed by conventional commercial methods.

GC-MS analyses were performed on a Hewlett Packard GC-6890 and 5939 Mass Spectrometer using electrospray ionization (ESI) in either positive or negative mode as indicated. The "mass calculated" for a molecular formula is the monoisotopic mass of the compound.

Flash column chromatography was performed using Merck silica gel 60. Chiral HPLC analysis was performed on a Hewlett Packard 1100 (Chiralcel AD column, EtOH/Hexanes=85/15, 1 mL/min).

Glassware was flame-dried prior to use.

Example 1 ee Determination

The ee of compounds of formula (I) was determined as follows: The ee of the compound of formula (Ia) was determined by chiral HPLC analysis of a derivative compound of formula (IIIa). The solution of compound of formula (Ia) (crude product before distillation, 100 mg, 0.46 mmol, 1 equiv), Et$_3$N (71 mg, 0.70 mmol, 1.5 equiv), and 4-nitrobenzoylchloride (0.13 g, 0.70 mmol, 1.5 equiv) in 10 mL of CH$_2$Cl$_2$ was stirred at rt for 16 h. The organic mixture was washed with brine, dried over MgSO$_4$ and concentrated. Column chromatography of the crude product with EtOAc/hexanes as eluent afforded the compound of formula (IIIa) as a white solid (100 mg, 0.27 mmol, 59%).

Example 2

1-Boc-pyrrolidine and racemic (±)-1-Boc-2-(2-hydroxyethyl)-pyrrolidine were prepared according to conventional procedures. See, for example, Manthorpe, J. M., Gleason, J. L., *J. Am. Chem. Soc.* 2001, 123, 2091-2092; and Beak, P., Lee, W. K., *J. Org. Chem.* 1993, 58,1109-1117. s-BuLi, (−)-sparteine, ethylene oxide, BF$_3$.Et$_2$O and 4-nitro-benzoylchloride were obtained form commercial sources (Aldrich). Anhydrous Et$_2$O was obtained from commercial sources (EM Science).

Example 3

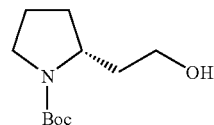

(2R)-2-(2-hydroxy-ethyl)-pyrrolidine-1-carboxylic acid tert-butyl ester, or (+)-(2R)-1-Boc-2-(2-hydroxy-ethyl)-pyrrolidine (−)-Sparteine (24.7 g, 105 mmol, 1.2 equiv) in 250 mL of Et$_2$O was cooled to −78° C. under N$_2$ and then 1-Boc-pyrrolidine (15 g, 88 mmol, 1.0 equiv) was added by syringe. After stirring at −78° C. for 10 min, s-BuLi (81 mL, 1.3 mol/L, 1.2 equiv) was added dropwise and the resulting mixture was stirred at −78° C. for 4 h. A solution of ethylene oxide (5.8 g, 130 mmol, 1.5 equiv) in 20 mL of Et$_2$O, which was pre-cooled to −78° C., was transferred to the previous flask via a cannula under N$_2$ and then BF$_3$.Et$_2$O (18.7.mL, 130 mmol, 1.5 equiv) was added dropwise over 30 min. GC-MS was used to monitor the reaction. After stirring at −78° C. for 2 h, the reaction mixture was slowly warmed to rt and water (5 mL) was carefully added to quench the reaction. The organic layer was washed with 5% aq. H$_3$PO$_4$ solution (100 mL) and brine, then dried over Na$_2$SO$_4$. Evaporation of the solvent afforded the crude product as a colorless oil (18.3 g, 85 mmol, 97%), which was distilled under vacuum to give the pure sample (15.5 g, 72 mmol, 83%). The optical rotation was compared with the literature value to assign the absolute configuration: Observed [α]$_D$=+21 (c=1.0, EtOH). Literature value for the S-enantiomer [α]$_D$=−57° (c=1.0, benzene) (see, for example, Leyendecker, F., Jesser, F., Laucher, D., *Tetrahedron Lett.* 1983, 24, 3513-3516). $^1$H NMR (500 MHz, CDCl$_3$): 4.40 (br s, 1H), 4.25-4.0 (m, 1H), 3.80-3.45 (m, 2H), 3.40-3.20 (m, 2H), 2.20-1.50 (m, 6H), 1.43 (s, 9H). $^{13}$C NMR (125 MHz, CDCl$_3$): 154.39, 77.72, 57.01, 51.43, 44.37, 36.30, 29.09, 26.36, 21.46. IR (neat): 2970.0 (w), 1668.4 (s), 1397.2 (s), 1365.4 (s), 1166.3 (s). EI-MS (70 eV): m/z (%): 215 (2, M$^+$); 170 (17, M$^+$—CH$_2$CH$_2$OH), 158 (8, M$^+$—C$_4$H$_9$), 142 (15, M$^+$—C$_4$H$_9$O), 114 (100, M$^+$—C$_4$H$_9$OCO). HRMS (ES): Calcd for C$_{11}$H$_{22}$NO$_3$ [M$^+$+H], 216.1600; found, 216.1610.

Example 3a (+)-(2R)-1-Boc-2-[2-(4-Nitro-benzoyloxy)-ethyl]-pyrrolidine

A solution of the title compound from Example 3 (crude product before distillation, 100 mg, 0.46 mmol, 1 equiv), Et$_3$N (71 mg, 0.70 mmol, 1.5 equiv) and 4-nitrobenzoyl chloride (0.13 g, 0.70 mmol, 1.5 equiv) in 10 mL of CH$_2$Cl$_2$ was stirred at room temperature for 16 h. The organic layer was washed with brine, dried over MgSO$_4$, filtered, and evaporated. Column chromatography of the crude product with EtOAc/hexanes as eluent afforded the title compound as a white solid (100 mg, 0.27 mmol, 59%). The racemic sample was prepared in the same way. $^1$H NMR (500 MHz, CDCl$_3$): 8.30-8.2 (m, 3, 2H), 8.21-8.16 (m, 2H), 4.50-4.30 (m, 2H), 4.10-3.85 (m, 1H), 3.50-3.20 (m, 2H), 2.40-1.60 (m, 6H), 1.44 (s, 9H). $^{13}$C NMR (125 MHz, CDCl$_3$): 144.21, 152.52, 133.59, 128.98, 128.62, 121.46, 77.58, 61.82, 52.59, (44.45, 44.02), (31.87, 31.26), (29.06, 28.24), 26.45, (21.78, 20.96). IR (neat): 2966.6 (w), 1724.9 (s), 1688.4 (s), 1528.7 (s), 1392.9 (s), 1275.3 (s). HRMS (ES): Calcd for C$_{18}$H$_{25}$N$_2$O$_6$ [M$^+$+H], 365.1713; found, 365.1716. Chiral HPLC analysis was performed on a Hewlett Packard 1100 (Chiralpak AD column 4.6×50 mm, mobile phase EtOH/Hexanes=85/15, Flow rate 1 mL/min). Retention times were 4.94 min (R-enantiomer) and 5.87 min (S-enantiomer), respectively. The ee of the product, determined by area integration was found to be 82%.

Example 4

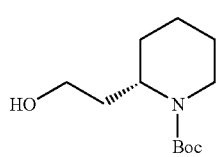

(2S)-2-(2-hydroxy-ethyl)-piperidine-1-carboxylic acid tert-butyl ester

This compound is prepared in a manner analogous to that described in Example 3, but 1-Boc-piperidine is used insead of 1-Boc-pyrrolidine, and (+)-sparteine surrogate is used instead of (−)-sparteine.

Example 5

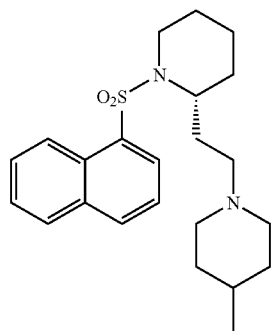

(2R)-2-[2-(4-methyl-1-piperidinyl)ethyl]-1-(1-naphthalenylsulfonyl)-piperidine

The compound prepared as in Example 4 undergoes a substitution reaction with naphthalene-1-sulfonyl chloride (2 equiv) in diisopropylethylamine and CH$_2$Cl$_2$ to generate 2-(2-chloro-ethyl)-1-(naphthalene-1-sulfonyl)-piperidine. Displacement of the chloro substituent with 4-methylpiperidine with sodium iodide as catalyst in the presence of K$_2$CO$_3$ and CH$_3$CN generates the title compound, a reported 5-HT$_7$ receptor modulator (see, for example, Lovell, P. J., Bromidge, S. M., Dabbs, S., Duckworth, D. M., Forbes, I. T., Jennings, A. J., King, F. D., Middlemiss, D. N.; Rahman, S. K., Saunders, D. V., Collin, L. L., Hagan, J. J., Riley, G. J., Thomas, D. R., *J. Med. Chem.* 2000, 43, 342-345).

Example 6

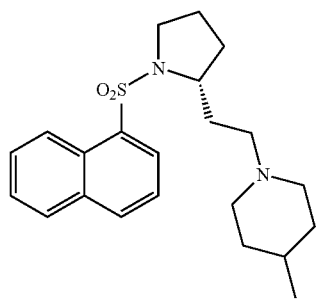

(2R)-2-[2-(4-methyl-1-piperidinyl)ethyl]-1-(1-naphthalenylsulfonyl)-pyrrolidine

The hydroxy group in the title compound in Example 3 is mesylated with methanesulfonyl chloride in the presence of Et$_3$N and CH$_2$Cl$_2$, and the OMs group is subsequently displaced with NaCN in DMF to convert it to to a nitrile, which is then transformed into a methylpiperidine side chain by hydrogenation over a Pt catalyst, such as PtO$_2$, in the presence of 4-methylpiperidine. The Boc protection is subsequently removed by using TFA in CH$_2$Cl$_2$, and the title compound is generated in a reaction with naphthalene-1-sulfonyl chloride in the presence of diisopropylethylamine and CH$_2$Cl$_2$. The Examples 7-20

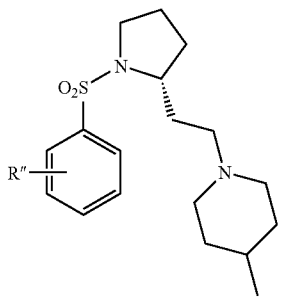

(2R)-1-[2-(1-phenyl-(2- and/or 3- and/or 4- and/or 5- and/or 6-R″)-sulfonyl-pyrrolidin-2-yl)-ethyl]-4-methyl-piperidine R″-derivatives Ex. 7: R″=halo; Ex. 8: R″=3-halo; Ex. 9: R″=3-Br; Ex. 10: R″=dihalo; Ex. 11: R″=3,4-dihalo; Ex. 12: R″=3,4-dichloro; Ex. 13: R″=alkyl; Ex. 14: R″=3-alkyl; Ex. 15: R″=3-methyl; Ex. 16: R″=alkoxy; Ex. 17: R″=3-alkoxy; Ex. 18: R″=3-methoxy; Ex. 19: R″=OH; Ex. 20: R″=3-hydroxy. The title compounds are prepared as described for the title compound in Example 6, provided that the last reaction step with naphthalene-1-sulfonyl chloride in Example 6 is modified as known in the art to introduce the specific substituted Ph given by R″ in each one of Examples 7-20. For reported 5-HT$_7$ receptor modulating activity, see, for example, the reference cited in Example 5.

Example 21

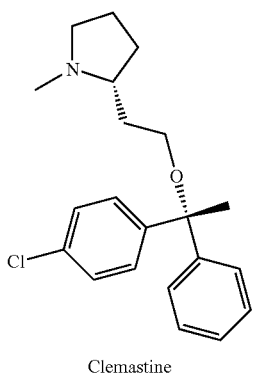

Clemastine

The title compound is given as an illustrative example of organic compounds that contain a diarylmethane moiety and a pyrrolidine moiety. The enantiomerically pure diarylethane moiety in such compounds is prepared by adding appropriately substituted aryllithiums to chiral azomethines. See, for example, Takahashi, H.; Suzuki, Y.; Hiori, T. *Chem. Pharm. Bull.* 1983, 31, 2183-2191. These moieties are then reacted with the pyrrolidine moiety in which the amine, when so desired, has been converted to a tertiary amine as shown in the title compound, and in which the hydroxyl group has been converted to a leaving group (for example, 2-(2-chloro-ethyl)-1-methyl-pyrrolidine). The chirality of this pyrrolidine moiety is generated according to the synthetic methods of the present invention as described herein. Implementation of this synthesis to other diarylmethanes that are bound to a pyrrolidine moiety can be implemented with the teachings provided herein and the ordinary skill in the art. Alternatively, diarylmethane moieties may be prepared for incorporation into similar molecules. For a more extensive discussion of the synthesis of diarylmethane moieties, see, for example, Stanchev, S., Rakovska, R., Berova, N., Snatzke, G., *Tetrahedron: Asymmetry* 1995, 6, 183-198.

Example 22

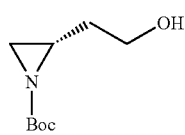

(2S)-2-(2-hydroxy-ethyl)-aziridine-1-carboxylic acid tert-butyl ester

This compound is prepared in a manner analogous to that described in Example 3, but 1-Boc-aziridine is used insead of 1-Boc-pyrrolidine.

Example 23

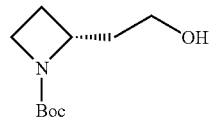

(2R)-2-(2-hydroxy-ethyl)-azetidine-1-carboxylic acid tert-butyl ester

This compound is prepared in a manner analogous to that described in Example 3, but 1-Boc-azetidine is used insead of 1-Boc-pyrrolidine.

Example 24

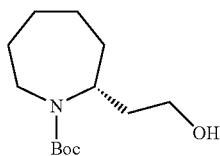

(2R)-2-(2-hydroxy-ethyl)-azepane-1-carboxylic acid tert-butyl ester

This compound is prepared in a manner analogous to that described in Example 3, but 1-Boc-hexahydroazepine is used insead of 1-Boc-pyrrolidine.

Example 25

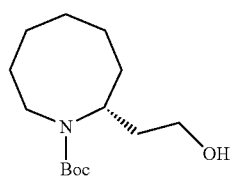

(2R)-2-(2-hydroxy-ethyl)-azocane-1-carboxylic acid tert-butyl ester

This compound is prepared in a manner analogous to that described in Example 3, but 1-Boc-azocane is used insead of 1-Boc-pyrrolidine.

Example 26

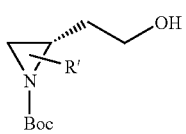

(2S)-2-(2-hydroxy-ethyl)-(3-R')-aziridine-1-carboxylic acid tert-butyl ester R'-derivatives R' in the title compound is one of alkyl, alkenyl, akynyl, alkoxy, aminoalkyl, thioalkyl, sulfonylalkyl, cycloalkyl, heterocyclyl, halo, and phenyl. These compounds are prepared in a manner analogous to that described in Example 22, wherein the aziridine structure is chosen with the appropriate substituent R'.

Example 27

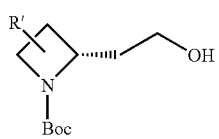

(2R)-2-(2-hydroxy-ethyl)-(3- and/or 4-R')-azetidine-1-carboxylic acid tert-butyl ester R'-derivatives R' in the title compound is at least one of alkyl, alkenyl, akynyl, alkoxy, aminoalkyl, thioalkyl, sulfonylalkyl, cycloalkyl, heterocyclyl, halo, and phenyl. These compounds are prepared in a manner analogous to that described in Example 23, wherein the azetidine structure is chosen with the appropriate substituent(s) R'.

Example 28

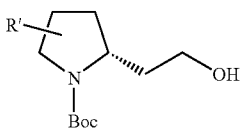

(2R)-2-(2-hydroxy-ethyl)-(3- and/or 4- and/or 5-R')-pyrrolidine-1-carboxylic acid tert-butyl ester R'-derivatives R' in the title compound is at least one of alkyl, alkenyl, akynyl, alkoxy, aminoalkyl, thioalkyl, sulfonylalkyl, cycloalkyl, heterocyclyl, halo, and phenyl. These compounds are prepared in a manner analogous to that described in Example 3, wherein the pyrrolidine structure is chosen with the appropriate substituent(s) R'.

Example 29

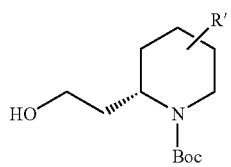

(2S)-2-(2-hydroxy-ethyl)-(3- and/or 4- and/or 5-R')-piperidine-1-carboxylic acid tert-butyl ester R'-derivatives R' in the title compound is at least one of alkyl, alkenyl, akynyl, alkoxy, aminoalkyl, thioalkyl, sulfonylalkyl, cycloalkyl, heterocyclyl, halo, and phenyl. These compounds are prepared in a manner analogous to that described in Example 4, wherein the piperidine structure is chosen with the appropriate substituent(s) R'.

Example 30

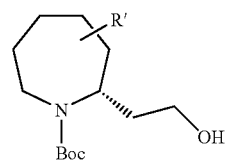

(2R)-2-(2-hydroxy-ethyl)-(3- and/or 4- and/or 5- and/or 6- and/or 7-R')-azepane-1-carboxylic acid tert-butyl ester R'-derivatives R' in the title compound is at least one of alkyl, alkenyl, akynyl, alkoxy, aminoalkyl, thioalkyl, sulfonylalkyl, cycloalkyl, heterocyclyl, halo, and phenyl. These compounds are prepared in a manner analogous to that described in Example 24, wherein the hexahydroazepine structure is chosen with the appropriate substituent(s) R'.

Example 31

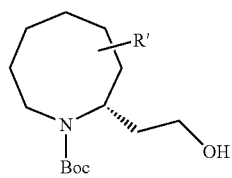

(2R)-2-(2-hydroxy-ethyl)-(3- and/or 4- and/or 5- and/or 6- and/or 7- and/or 8-R')-azepane-1-carboxylic acid tert-butyl ester R'-derivatives R' in the title compound is at least one of alkyl, alkenyl, akynyl, alkoxy, aminoalkyl, thioalkyl, sulfonylalkyl, cycloalkyl, heterocyclyl, halo, and phenyl. These compounds are prepared in a manner analogous to that described in Example 25, wherein the azocane structure is chosen with the appropriate substituent(s) R'.

Example 32

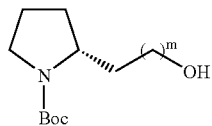

(2R)-2-(2-hydroxy-$C_{m+1}$alkyl)-pyrrolidine-1-carboxylic acid tert-butyl ester Title compounds are prepared as described in Example 3, with a strained cyclic ether according to this invention and optionally a homologation synthetic step to extend the carbon chain, so that m>1.

Example 33

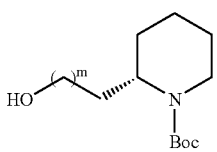

(2S)-2-(2-hydroxy-$C_{m+1}$alkyl)-piperidine-1-carboxylic acid tert-butyl ester

Title compounds are prepared as described in Example 4, with a strained cyclic ether according to this invention and optionally a homologation synthetic step to extend the carbon chain, so that m>1.

Example 34

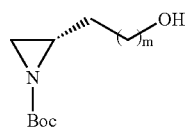

(2S)-2-(2-hydroxy-$C_{m+1}$alkyl)-aziridine-1-carboxylic acid tert-butyl ester

Title compounds are prepared as described in Example 22, with a strained cyclic ether according to this invention and optionally a homologation synthetic step to extend the carbon chain, so that m>1.

Example 35

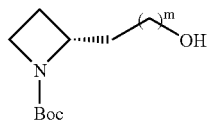

(2R)-2-(2-hydroxy-$C_{m+1}$alkyl)-azetidine-1-carboxylic acid tert-butyl ester

Title compounds are prepared as described in Example 23, with a strained cyclic ether according to this invention and optionally a homologation synthetic step to extend the carbon chain, so that m>1.

Example 36

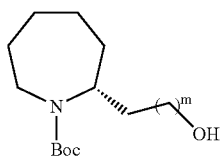

(2R)-2-(2-hydroxy-$C_{m+1}$alkyl)-azepane-1-carboxylic acid tert-butyl ester

Title compounds are prepared as described in Example 24, with a strained cyclic ether according to this invention and optionally a homologation synthetic step to extend the carbon chain, so that m>1.

Example 37

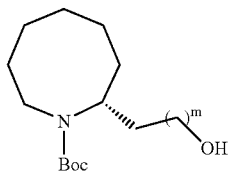

(2R)-2-(2-hydroxy-$C_{m+1}$alkyl)-azocane-1-carboxylic acid tert-butyl ester

Title compounds are prepared as described in Example 25, with a strained cyclic ether according to this invention and optionally a homologation synthetic step to extend the carbon chain, so that m>1.

Example 38

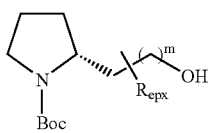

(2R)-2-(2-hydroxy-$R_{epx}$-substituted $C_{m+1}$alkyl)-pyrrolidine-1-carboxylic acid tert-butyl ester Title compounds are prepared as described in Examples 3 and 32, but instead of the strained cyclic ethers named therein, the following strained cyclic ethers are used. Example 62: $R_{epx}$-substituted oxirane (m=1). Example 63: $R_{epx}$-substituted oxetane (m2). Embodiments with greater m-values are made by homologation synthesis with suitable $R_{epx}$ substituents. Wherein $R_{epx}$ substitution is defined above, and the $R_{epx}$-substituted strained cyclic ethers are as follows:

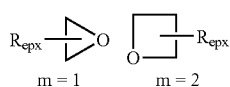

Example 39

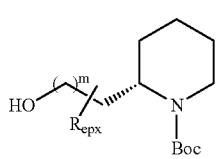

(2S)-2-(2-hydroxy-$R_{epx}$-substituted $C_{m+1}$alkyl)-piperidine-1-carboxylic acid tert-butyl ester Title compounds are prepared as described in Examples 4 and 33, but instead of the strained cyclic ethers named therein, the following strained cyclic ethers are used. $R_{epx}$-substituted oxirane (m=1). $R_{epx}$-substituted oxetane (m=2). Embodiments with greater m-values are made by homologation synthesis with suitable $R_{epx}$ substituents.

Example 40

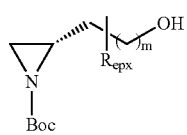

(2S)-2-(2-hydroxy-$R_{epx}$-substituted $C_{m+1}$alkyl)-aziridine-1-carboxylic acid tert-butyl ester Title compounds are prepared as described in Examples 22 and 34, but instead of the strained cyclic ethers named therein, the following strained cyclic ethers are used. $R_{epx}$-substituted oxirane (m=1). $R_{epx}$-substituted oxetane (m=2). Embodiments with greater m-values are made by homologation synthesis with suitable $R_{epx}$ substituents.

Example 41

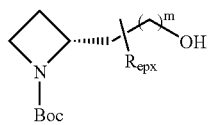

(2R)-2-(2-hydroxy-$R_{epx}$-substituted $C_{m+1}$alkyl )-azetidine-1-carboxylic acid tert-butyl ester Title compounds are prepared as described in Examples 23 and 35, but instead of the strained cyclic ethers named therein, the following strained cyclic ethers are used. $R_{epx}$-substituted oxirane (m=1). $R_{epx}$-substituted oxetane (m=2). Embodiments with greater m-values are made by homologation synthesis with suitable $R_{epx}$ substituents.

Example 42

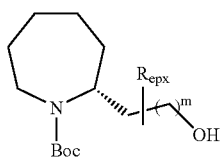

(2R)-2-(2-hydroxy-$R_{epx}$-substituted $C_{m+1}$alkyl)-azepane-1-carboxylic acid tert-butyl ester Title compounds are prepared as described in Examples 24 and 36, but instead of the strained cyclic ethers named therein, the following strained cyclic ethers are used. $R_{epx}$-substituted oxirane (m=1). $R_{epx}$-substituted oxetane (m=2). Embodiments with greater m-values are made by homologation synthesis with suitable $R_{epx}$ substituents.

Example 43

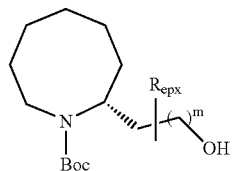

(2R)-2-(2-hydroxy-$R_{epx}$-substituted $C_{m+1}$alkyl)-azocane-1-carboxylic acid tert-butyl ester Title compounds are prepared as described in Examples 31 and 37, but instead of the strained cyclic ethers named therein, the following strained cyclic ethers are used. $R_{epx}$-substituted oxirane (m=1). $R_{epx}$-substituted oxetane (m=2). Embodiments with greater m-values are made by homologation synthesis with suitable $R_{epx}$ substituents.

Example 44

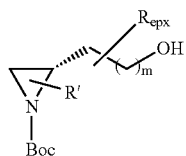

(2S)-2-(2-hydroxy-$R_{epx}$-substituted $C_{m+1}$alkyl)-(3-R')-aziridine-1-carboxylic acid tert-butyl ester R'-derivatives Title compounds are prepared as described in Example 26, but instead of the strained cyclic ether used therein (ethylene oxide, m=1), the following strained cyclic ethers are used: oxetane (m=2). Embodiments with greater m-values are made by homologation synthesis with suitable $R_{epx}$ substituents. Compounds with an $R_{epx}$-substituted side chain are illustrated by the following examples. $R_{epx}$-substituted oxirane (m=1). $R_{epx}$-substituted oxetane (m=2). To reduce the number of displayed chemical structures, note that $R_{epx}$ is shown in the structures displayed for Examples 44-49 whether such substituent is present or not in the actual title compound. One of ordinary skill in the art will recognize that H is taken instead of $R_{epx}$ when such substituent is not present.

Example 45

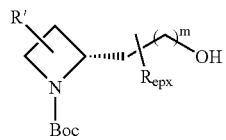

(2R)-2-(2-hydroxy-$R_{epx}$-substituted $C_{m+1}$alkyl)-(3- and/or 4-R')-azetidine-1-carboxylic acid tert-butyl ester R'-derivatives Title compounds are prepared as described in Example 27, but instead of the strained cyclic ether used therein (ethylene oxide, m=1), the following strained cyclic ethers are used: oxetane (m=2). Embodiments with greater m-values are made by homologation synthesis with suitable $R_{epx}$ substituents. Compounds with an $R_{epx}$-substituted side chain are illustrated by the following examples. $R_{epx}$-substituted oxirane (m=1). $R_{epx}$-substituted oxetane (m=2).

Example 46

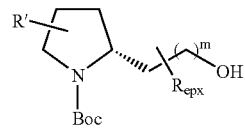

(2R)-2-(2-hydroxy-$R_{epx}$-substituted $C_{m+1}$alkyl)-(3- and/or 4- and/or 5-R')-pyrrolidine-1-carboxylic acid tert-butyl ester R'-derivatives Title compounds are prepared as described in Example 28, but instead of the strained cyclic ether used therein (ethylene oxide, m=1), the following strained cyclic ethers are used: oxetane (m=2). Embodiments with greater m-values are made by homologation synthesis with suitable $R_{epx}$ substituents. Compounds with an $R_{epx}$-substituted side chain are illustrated by the following examples. $R_{epx}$-substituted oxirane (m=1). $R_{epx}$-substituted oxetane (m=2).

Examples 47

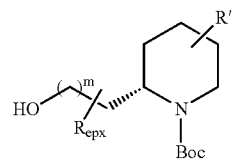

(2S)-2-(2-hydroxy-$R_{epx}$-substituted $C_{m+1}$alkyl)-(3- and/or 4- and/or 5- and/or 6-R')-piperidine-1-carboxylic acid tert-butyl ester R'-derivatives Title compounds are prepared as described in Example 29, but instead of the strained cyclic ether used therein (ethylene oxide, m=1), the following strained cyclic ethers are used: oxetane (m=2). Embodiments with greater m-values are made by homologation synthesis with suitable $R_{epx}$ substituents. Compounds with an $R_{epx}$-substituted side chain are illustrated by the following examples. $R_{epx}$-substituted oxirane (m=1). $R_{epx}$-substituted oxetane (m=2).

Example 48

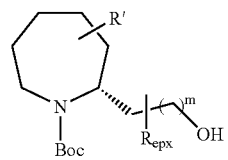

(2R)-2-(2-hydroxy-$R_{epx}$-substituted $C_{m+1}$alkyl)-(3- and/or 4- and/or 5- and/or 6- and/or 7-R')-azepane-1-carboxylic acid tert-butyl ester R'-derivatives Title compounds are prepared as described in Example 30, but instead of the strained cyclic ether used therein (ethylene oxide, m=1), the following strained cyclic ethers are used:

oxetane (m=2). Embodiments with greater m-values are made by homologation synthesis with suitable $R_{epx}$ substituents. Compounds with an $R_{epx}$-substituted side chain are illustrated by the following examples. $R_{epx}$-substituted oxirane (m=1). $R_{epx}$-substituted oxetane (m=2).

Example 49

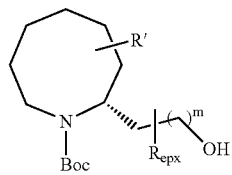

(2R)-2-(2-hydroxy-$R_{epx}$-substituted $C_{m+1}$alkyl)-(3- and/or 4- and/or 5- and/or 6- and/or 7- and/or 8-R')-azocane-1-carboxylic acid tert-butyl ester Title compounds are prepared as described in Example 31, but instead of the strained cyclic ether used therein (ethylene oxide, m=1), the following strained cyclic ethers are used: oxetane (m=2). Embodiments with greater m-values are made by homologation synthesis with suitable $R_{epx}$ substituents. Compounds with an $R_{epx}$-substituted side chain are illustrated by the following examples. $R_{epx}$-substituted oxirane (m=1). $R_{epx}$-substituted oxetane (m=2).

Example 50

Enantiocomplementary Synthesis

This example collectively refers to the prior examples given herein. Each one of the foregoing examples can be performed with the teachings provided herein by using, instead of the chiral diamine that is used in each of the foregoing examples, the enantiocomplementary chemical species. This is to say, (+)-sparteine or (+)-sparteine surrogate is used instead of (−)-sparteine, or (−)-sparteine is used instead of (+)-sparteine or (+)-sparteine surrogate. The synthesis in any of these enantiocomplementary syntheses proceeds as described in each of the foregoing examples, with expected similar enatioselectivity extent, but predominantly generating the enantiocomplementary final product: predominantly generating the R product where the S product is generated in the corresponding foregoing example(s), or predominantly generating the S product where the R product is generated in the corresponding foregoing example(s).

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. These other embodiments are also within the scope of the invention.

What is claimed is:

1. A method for making a chiral alkylated derivative of a nitrogen-containing heterocycle, comprising: incorporating into a medium with an α-substitutable-N-heterocycle at least an organometallic compound, a chiral diamine, a strained cyclic ether, and a Lewis acid, wherein:

the α-substitutable-N-heterocycle is selected from the group consisting of aziridine, azetidine, azepane, pyrrolidine, piperidine, hexahydroazepine, azocane, imidazolidine, pyrazolidine, hexahydropyridazine, hexahydropyrimidine, piperazine, and mixtures thereof, and forms of such heterocycles that have at least one protected amino group;

the organometallic compound is an organolithium; and the chiral diamine is (+)-sparteine, (−)-sparteine, (+)-sparteine surrogate, or a salt or stereoisomer thereof.

2. A method as in claim 1, wherein said chiral diamine, said organometallic compound, and said α-substitutable-N-heterocycle form in said medium a N-heterocycle-metal-chiral diamine complex.

3. A method as in claim 2, wherein said medium is temperature-controlled.

4. A method as in claim 3, wherein said medium is at a temperature such that said complex is thermally stable.

5. A method as in claim 1, wherein wherein said medium is at a temperature in the range from about −75° C. to about −100° C.

6. A method as in claim 1, wherein the medium initially contains said α-substitutable-N-heterocycle and said chiral diamine, and wherein said incorporating comprises incorporating the organometallic compound, followed by incorporating the strained ether and the Lewis acid.

7. A method as in claim 6, wherein said strained cyclic ether is incorporated before said Lewis acid is incorporated.

8. A method as in claim 1, wherein said α-substitutable-N-heterocycle is one of aziridine, azetidine, pyrrolidine, piperidine, hexahydroazepine, azocane, and mixtures thereof.

9. A method as in claim 8, wherein said α-substitutable-N-heterocycle has its >NH member protected.

10. A method as in claim 1, wherein said α-substitutable-N-heterocycle is one of imidazolidine, pyrazolidine, hexahydropyridazine, hexahydropyrimidine, piperazineaziridine, and mixtures thereof.

11. A method as in claim 10, wherein said α-substitutable-N-heterocycle has at least one of its >NH members protected.

12. A method as in claim 1, wherein said α-substitutable-N-heterocycle is one of 1-Boc-aziridine, 1-Boc-azetidine, 1-Boc-pyrrolidine, 1-Boc-piperidine, 1-Boc-hexahydroazepine, 1-Boc-azocane, and mixtures thereof.

13. A method as in claim 1, wherein said α-substitutable-N-heterocycle is 1-Boc-pyrrolidine.

14. A method as in claim 1, wherein said strained cyclic ether is an epoxide.

15. A method as in claim 14, wherein said epoxide is one of oxirane, oxirene, 1,2-epoxypropane, and 2,3-epoxybutane.

16. A method as in claim 1, wherein said strained cyclic ether is 9,10-epoxy-9,10-dihydroanthracene.

17. A method as in claim 1, wherein said strained cyclic ether is one of 1-oxa-spiro-[2.2]pentane; 2-oxa-bicyclo [1.1.0]butane, 5-oxa-bicyclo[2.1.0]pentane, 6-oxa-bicyclo [3.1.0]hexane, 7-oxa-bicyclo[4.1.0]heptane, 8-oxa-bicyclo [5.1.0]octane, 9-oxa-bicyclo[6.1.0]nonane, 2-oxa-bicyclo [1.1.1]pentane, 2-oxa-tricyclo[1.1.1.0$^{1,3}$]pentane, 5-oxa-bicyclo[2.1.1]hexane, 5-oxa-tricyclo[2.1.1.0$^{1,4}$]hexane, 8-oxa-tricyclo[3.2.1$^{1,5}$]octane, 7-oxa-bicyclo[2.2.1]heptane, 7-oxa-tricyclo[2.2.1$^{1,4}$]heptane, 2-oxa-bicyclo[2.2.2]oct-1 (7)-ene, 2-oxa-bicyclo[2.2.2]oct-4(8)-ene, 2-oxa-tricyclol [2.2.2.0$^{1,4}$]octane, 11-oxa-bicyclo[4.4.1]undec-1(10)-ene, 2-oxa-tricyclo[3.3.1.1$^{3,7}$]dec-1(9)-ene, and 3-oxaquadricyclane.

18. A method as in claim 1, wherein said strained cyclic ether is one of oxirane, oxirene, and oxetane.

19. A method as in claim 1, wherein said organometallic compound is alkyllithium.

20. A method as in claim 1, wherein said organometallic compound is s-BuLi.

21. A method as in claim 1, wherein said Lewis acid is $BF_3$.

22. A method as in claim 21, wherein said Lewis acid is $BF_3$ and said Lewis acid is provided as $BF_3.Et_2O$.

23. A method as in claim 1, wherein said medium is at a temperature in the range from about −78° C. to about −100° C.

24. A method as in claim 23, wherein said temperature is in the range from about −80° C. to about −100° C.

25. A method as in claim 23, wherein said temperature is in the range from about 75° C. to about −90° C.

26. A method as in claim 23, said temperature is in the range from about −75° C. to about −80° C.

27. A method as in claim 23, wherein said temperature is about −78° C.

28. A method as in claim 1, wherein said medium is provided by one of $Et_2O$, TBME, dimethyl ether, dipropyl ether, and mixtures thereof.

29. A method as in claim 1, wherein said medium is provided by the solvent $Et_2O$.

30. A mehod as in claim 1, wherein said Lewis acid is a $BF_3$-containing Lewis acid, and said incorporating comprises incorporating said strained cyclic ether, and subsequently adding said Lewis acid.

31. A method as in claim 1, wherein said incorporating comprises incorporating said strained cyclic ether, and subsequently adding $BF_3.Et_2O$.

32. A method as in claim 1, wherein said strained cyclic ether is ethylene oxide, and said incorporating comprises incorporating said strained cyclic ether, and subsequently adding said Lewis acid.

33. A method as in claim 1, wherein said strained cyclic ether is ethylene oxide, and said incorporating comprises incorporating said strained cyclic ether, and adding subsequently $BF_3.Et_2O$.

34. A method as in claim 1, wherein said α-substitutable-N-heterocycle has an amino group that is protected with a protection group, wherein said protection group has at least one of an alkanoyl group, an alcoxycarbonyl group, an aroyl group, a phthaloyl group, an arylmethoxycarbonyl group, and a pivaloyl group.

35. A method as in claim 1, wherein said ct-substitutable-N-heterocycle comprises 1-Boc-pyrrolidine, said organometallic compound comprises s-BuLi, said chiral diamine comprises (−)-sparteine, said strained cyclic ether comprises ethylene oxide, said Lewis acid comprises $BF_3.Et_2O$, and said medium comprises $Et_2O$.

36. A method as in claim 1, wherein said ct-substitutable-N-heterocycle is 1-Boc-pyrrolidine, said organometallic compound is s-BuLi, said chiral diamine is (−)-sparteine, said strained cyclic ether is ethylene oxide, said Lewis acid is $BF_3.Et_2O$, and said medium is provided by the solvent $Et_2O$.

* * * * *